United States Patent
Ginty et al.

(10) Patent No.: US 6,428,965 B1
(45) Date of Patent: *Aug. 6, 2002

(54) SCREENING ASSAYS FOR THE INTERACTION OF SEMAPHORINS AND NEUROPILINS

(75) Inventors: David D. Ginty, Columbia; Alex L. Kolodkin, Baltimore, both of MD (US)

(73) Assignee: The Johns Hopkins University, Baltimore, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/116,473

(22) Filed: Jul. 16, 1998

Related U.S. Application Data
(60) Provisional application No. 60/052,762, filed on Jul. 17, 1997.

(51) Int. Cl.[7] ............ G01N 33/53; G01N 33/537; G01N 33/566; G01N 33/567; C12Q 1/42
(52) U.S. Cl. ............ 435/7.1; 435/7.2; 435/7.21; 435/7.8; 435/21
(58) Field of Search ............ 435/7.1, 7.2, 7.21, 435/7.8, 21

(56) References Cited

U.S. PATENT DOCUMENTS

| | | | |
|---|---|---|---|
| 5,639,856 A | | 6/1997 | Goodman et al. |
| 5,766,882 A | * | 6/1998 | Falkner et al. |
| 6,054,293 A | * | 4/2000 | Tessier-Lavigne et al. |

FOREIGN PATENT DOCUMENTS

| | | |
|---|---|---|
| WO | WO 95 07706 | 3/1995 |
| WO | WO 96/30404 | 10/1996 |
| WO | WO 97/14424 | 4/1997 |

OTHER PUBLICATIONS

Luo et al., *Cell*, vol. 75, pp. 217–227, 1993.*
Kawakami, A. et al.: "Developmentally Regulated Expression of a Cell Surface Protein, Neuropilin, in the Mouse Nervous System" Journal of Neurobiology, vol. 29, 1996, pp. 1–17.
Chen, H. et al.: "Neuropilin–2, a Novel Member of the Neuropilin Family, Is a High Affinity Receptor for the Semaphorins Sema E and Sema IV but Not Sema III," (published erratum appears in Neuron 1997, Sep.;19(3):559. Neuron, (1997 Sep.) 19(3)547–59.
Kolodkin, A. et al., "Steering Clear of Semaphorins: Neuropilins Sound the Retreat" Neuron, vol. 19, 1159–1162, 1997.
He, Z. et al.: "Neuropilin is a Receptor for the Axonal Chemorepellent Semaphorin III" Cell, (Aug. 22, 1997) 90(4) pp. 739–51.
Kolodkin, A.L. et al.: "Neuropilin is a Semaphorin III Recept r" Cell, (Aug. 22, 1997) 90(4) pp. 753–62.
Tessier–Lavigne, Marc et al.: "The Molecular Biology of an Axon Guidance" Science (Washington, DC) (1996), 274(5290), pp. 1123–1133.
Culotti, Joseph G. et al.: "Functions of Netrins and Semaphorins in Axon Guidance" Curr. Opin. Neurobiol. (1996), 6(1), pp. 81–8.
Kolodkin, Alex L.: "Semaphorins: mediators of repulsive growth cone guidance" Trends Cell Biol., 6(1), pp. 15–22, 1996.
Takagi, et al.: "Expression of a Cell Adhesion Molecule, Neuropilin, in the Developing Chick Nervous System" Developmental Biology, vol. 170, 1995, pp. 207–22.
Alex L. Kolodkin et al. "The semaphorin Genes Encode a Family of Transmembrane and Secreted Growth Cone Guidance Molecules" Cell, vol. 75, 1389–1399, Dec. 31, 1993.
David J. Matthes et al., "Semaphorin II Can Function as a Selective Inhibitor of Specific Synaptic Arborizations" Cell, vol. 81, 631–639, May 19, 1995.
Elizabeth K. Messersmith et al. "Semaphorin III Can Function as a Selective Chemorepellent to Pattern Sensory Projections in the Spinal Cord" Neuron, vol. 14, 949–959, May, 1995.
Alex L. Kolodkin, "Growth cones and the cues that repel them" Trends Neurosci. (1996) 19, 507–513.
Alex L. Kolodkin, "Semaphorins: mediators of repulsive growth cone guidance" trends in Cell Biology (vol. 6), Jan. 1996, pp. 15–21.
Takashi Kitsukawa et al. "Overexpression of a membrane protein, neuropilin, in chimieric mice cuases anomalies in the cardiovascular system nervous system and limbs" Development 121, 4309–4318 (1995).
Shay Soker et al. "Neuropilin–1 is Expressed by Endothelial and Tumor Cells as an Isoform–Specific Receptor for Vascular Endothelial Growth Factor" Cell, vol. 92, 735–745, May 20, 1998.

* cited by examiner

Primary Examiner—Gary L. Kunz
Assistant Examiner—Stephen Gucker
(74) Attorney, Agent, or Firm—Banner & Witcoff, Ltd.

(57) ABSTRACT

The semaphorin family contains a large number of plylogenetically conserved proteins and includes several members that have been shown to function in repulsive axon guidance. Semaplorin III (Sema III) is a secreted protein that in vitro causes neuronal growth cone collapse and chemorepulsion of neurites, and is required in vivo for correct sensory afferent innervation and other aspects of development. The mechanism of Sema III function, however, is unknown. Here, we report that neuropilin, a type I transmembrane protein, is a Sema III receptor. We also describe the identification of neuropiln-2, a related neuropilin family member, and show that neuropilin and neuropilin-2 are expressed in overlapping, yet distinct, populations of neurons in the rat embryonic nervous system.

25 Claims, 8 Drawing Sheets

FIG. 1A
FIG. 1B
FIG. 1C
FIG. 1D
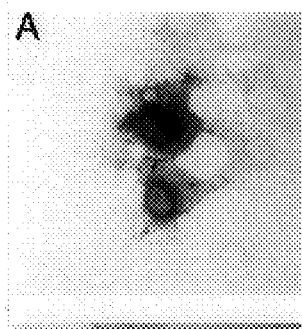
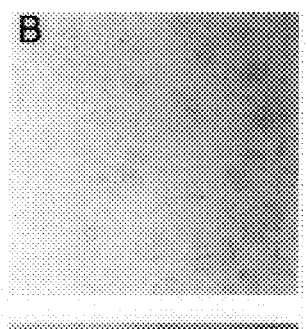
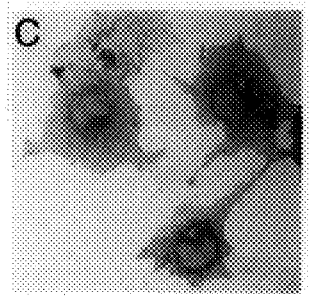
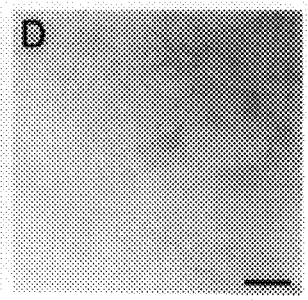
FIG. 1E
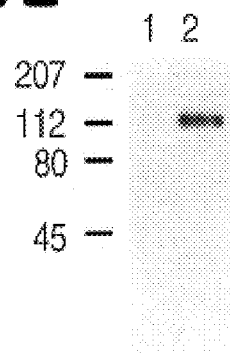
FIG. 1F
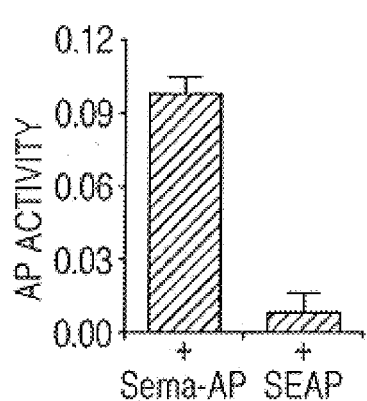

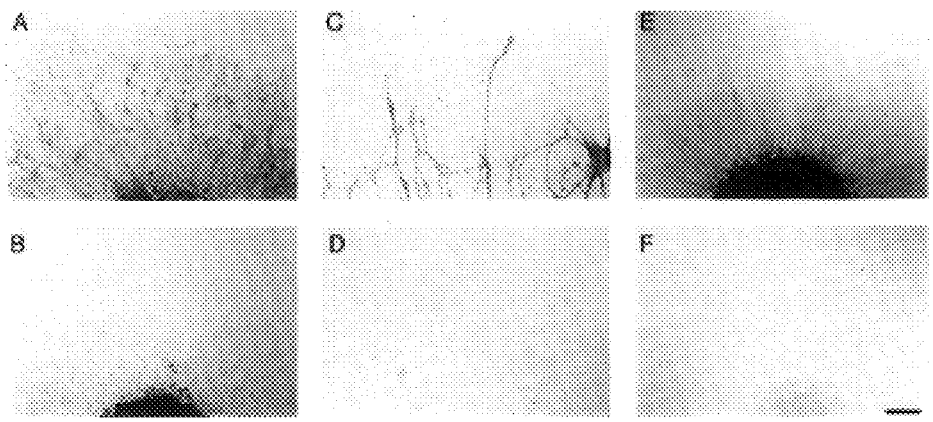

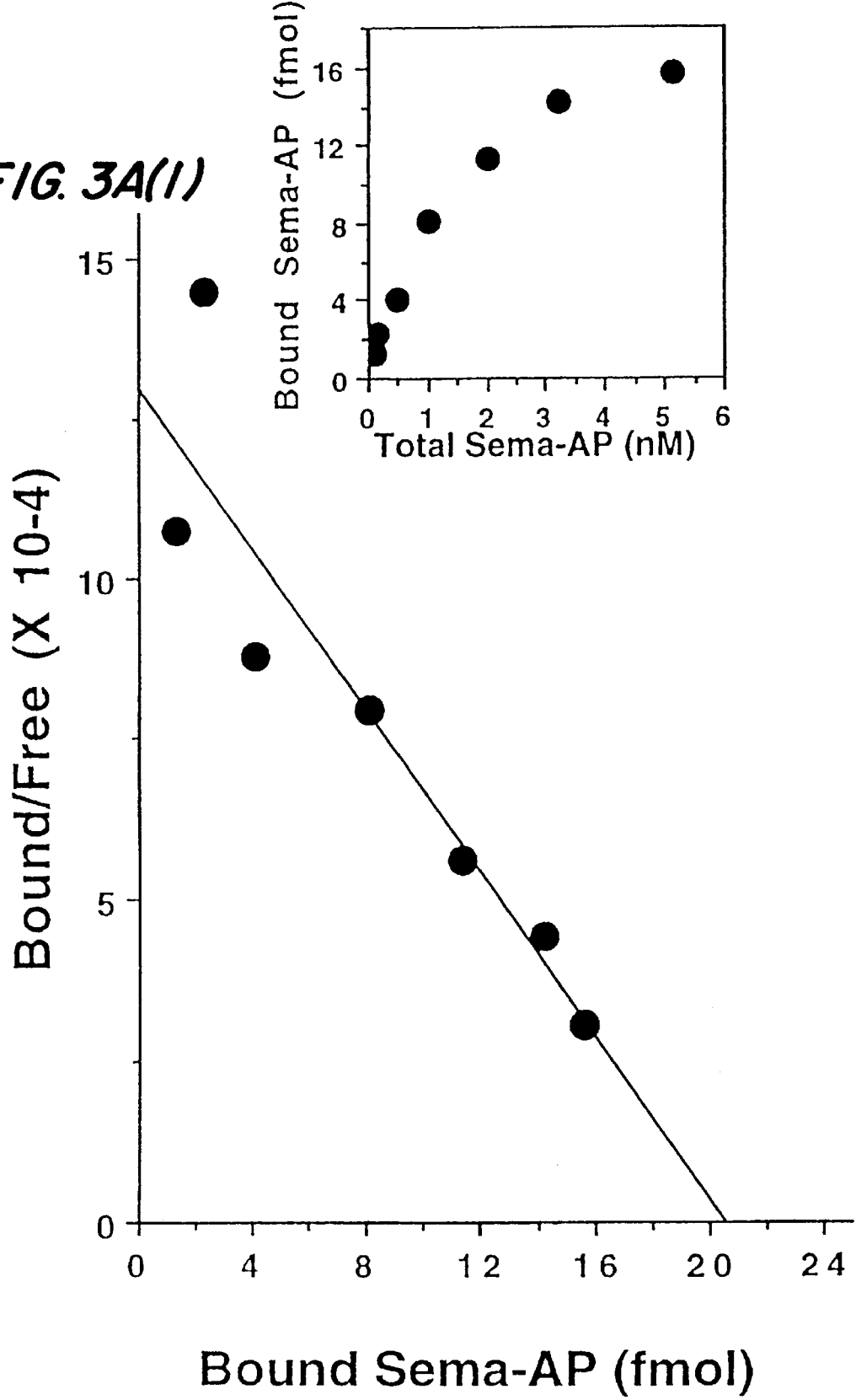

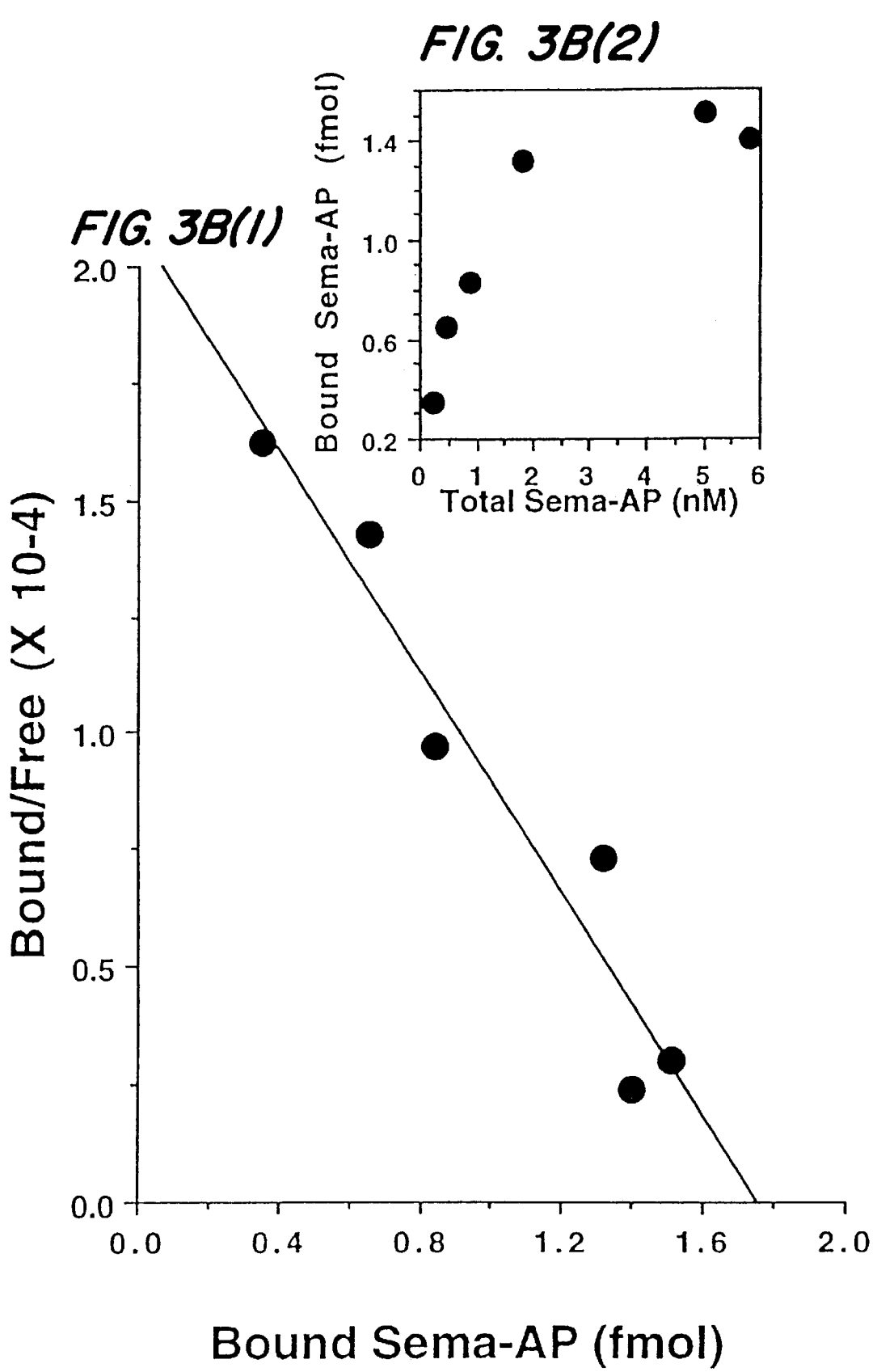

FIG. 5A

| | | |
|---|---|---|
| neuropilin-2 | MDMFPLTWIFLALYFSGHKVRSQQDPPCGGRLNSKDAGYITSPGYPQDYPSHQNCEWMVYAPEPNQKIVLNFNPH | 75 |
| neuropilin | MER-GLPLLCATLALALAGAFRSDKCGGTIKIENPGYLTSPGYPHSYHPSEKCEWLIQAPEPYQRIMINFNPH | 74 |
| neuropilin-2 | FEIEKHDCKYDFIEIRDGDSESADLLGKHCGNIAPPTIISSGSVLYIKFISDYARQGAGFSLRYEIFKIGSEDCS | 150 |
| neuropilin | FDLEDRDCKYDYVEVIDGENEGGRLWGKFCGKIAPSPVVSSGPFLFIKFMSDYETHGAGFSIRYEIFKRGPEI-CS | 148 |
| neuropilin-2 | KNFTSPNGIIESPGFPEKYPHNLDCTFTILAKPRMETILQFLTFDLEHDPLQVGEGDCKYDWLDIWDGIPHVGPL | 225 |
| neuropilin | QNYTAPIGMIKSPGFPEKYPNSLECTYIIFAPKMSEIILEFESFDLEQDSNPPGGVFCRYDRLEIIWDGFPEVGPH | 223 |
| neuropilin-2 | IGKYCGIKTPSKLRSSIGILSLTFHTDMAWAKDGFSARYYLVHQEPPENFDCNAPLGMESGRIVNEQISASSTFS | 300 |
| neuropilin | IGRYCGQKTPGRIRSSSGILSMVFMTDSAIAKEGFSANYSVLQSSISEDFKCMEALGMESGEIHSDQIIASSQY- | 297 |
| neuropilin-2 | DGRMTPQQSRLHGDDNGWTPNVDSNKEYLQVDLRFLTMLTAIATQGAISRETQKGYYVKSYKLEVSINGEDWMVY | 375 |
| neuropilin | GTNMSVERSRLNYPENGWTPGEDSYREWIQVDLGLLRFVTAVGTQGAISKETKKKYYVKIMRVDISSNGEDWITL | 372 |
| neuropilin-2 | RHGKNHKVFQANNDATELVLNKLHTPLLTRFIRIRPQTWHLGIALRLELFGCRVTDAPCSNMLGMLSGLIADIQI | 450 |
| neuropilin | KEGNKAIIFQGNTNPTDWVFGVFPKPLITRFMRIKPASWETGISMRFEVYGCKITDYPCSGMLGMVSGLISDSQI | 447 |
| neuropilin-2 | SASSTREYLWSPSAARLVSSRSGWFPRNPQAQPGEEWLQVDLGTPKIVKGVIIQGARGGDSITAMEARAFVRKFK | 525 |
| neuropilin | TASHQGDRNWMPENIRLVISRIGWALPPSPHPYINEWLQVDLGDEKIVRGVIIQGGKHRENKVFMRKFK | 516 |
| neuropilin-2 | VSYSLNGKDWEYIQDPRTQQPKLFEGNMHYDTPDIRRFEPNPAQYVRWYPERWSPAGIGMRLEVLGCD--WTDSK | 598 |
| neuropilin | IAYSNNGSDWKMIMDDSKRKAKSFEGNNNYDTPELRAFIPLSTRFIRIYPERATHSGLGLRMELLGCEVEVPTAG | 591 |
| neuropilin-2 | PTVETLGPTVKSEE-------ITTPYPMDEDATE-CGENCSFEDK-DLQLPS-GFNCNFDF-PEEIT-CGMMYD | 660 |
| neuropilin | PITPNGNPVDECDDDQANCHSGTGDDFQLTGGTIVLATEKPTIIDSTIQSEFPTYGFNCEFGWGSHKTFCHMEHD | 666 |
| neuropilin-2 | RAKWLDSTWISSANPNDRTFPDDKNFLKLQSDGGREGQFGRLISPPVHLPRSPVCMEFQYQAMGGHGVALDM-VR | 734 |
| neuropilin | SHAQLRWRVLTSKTGPIQDHTGDGNFIYSQADENQKGKVARLVSPMVYSQSSAHCMIFWYHMSGSHVGTLRVKLH | 741 |
| neuropilin-2 | EARQE--SKLLMVIREDQGSEWKHGRILLPSYDMEYQIVFEGVIGKGRSGEISIDDIRISTDVPLENCMEPISAF | 807 |
| neuropilin | YQKPEEYDQLVWWVVGHQGDHWKEGRVLLHKSLKLYQVIFEGEIGKGNLGGIAVDDISINNHIPQEDCAKP-TDL | 815 |
| neuropilin-2 | AVDIPEIHGGEGYEDEIDDDYEGDWNNSSSTSGAGSPSSGKEKSWLYTLDPILITIIAMSSLGVLLGAICAGLLL | 882 |
| neuropilin | DKKNTEIKID---ETGSTPGYEEGKGDKNISRKPGNV-------LKTLDPILITIIAMSALGVLLGAVCGVVLY | 879 |
| neuropilin-2 | YCICSYSGLSSRSCTTLENYNFELYDGLK-HKVKINHQKCCSEA | 925 |
| neuropilin | -CACWHHNGMSERNLSALENYNFELVDGVKLKKDKLNPQSNYSEA | 922 |

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 3371 base pairs
      (B) TYPE: nucleic acid
      (C) STRANDEDNESS: single
      (D) TOPOLOGY: linear (xi) SEQUENCE DESCRIPTION: SEQ ID NO:1:

```
TAGATCCCCG GGCTGCAGGA ATTCTGCGGC CGCAGACCAT ACACGCGTTT GGGTTTGAAG     60

AGGAAACTGG TCTCCGCTTC CCCAGCTTGC TCCCTCTTTG CTGATTTCAG GGGCTATCTC    120

TTAGTGAGGT GGAGATATTC CAGCAAGAAT AAAGGTGAAG GCAGACGGAC CTCCAGGACG    180

CAGGAGGAAA ACGCTGATCA TTAGAGACCT TTGCAGAAGA CACCACAAGG AAGAAAATTA    240

GAGAGGAAAA ACACAAAGAC ATTATACGAG ATCCCACCAA CCTAGCCCTG GAGAGAGCCT    300

CTCTGTCAAA AATGGATATG TTTCCTCTCA CCTGGATTTT CTTAGCTCTG TACTTTTCGG    360

GACACAAAGT GAGAAGCCAG CAAGATCCGC CCTGCGGAGG TCGGCTGAAT TCCAAAGATG    420

CTGGCTATAT CACTTCCCCA GGTTACCCCC AGGACTATCC CTCTCACCAG AACTGTGAGT    480

GGGTTGTCTA TGCCCCCGAA CCCAACCAGA AGATTGTCCT CAACTTCAAC CCTCACTTTG    540

AAATCGAGAA GCATGACTGC AAGTATGACT TCATTGAGAT TCGGGATGGA GACAGTGAGT    600

CAGCTGACCT CCTGGGCAAG CACTGTGGGA ACATTGCCCC TCCCACCATC ATCTCTTCCG    660

GCTCCGTGTT ATATATCAAG TTCACATCAG ACTACGCCCG GCAGGGGGCA GGTTTCTCCC    720

TACGCTATGA GATCTTCAAA ACAGGCTCTG AAGATTGTTC CAAGAACTTT ACAAGCCCCA    780

ATGGGACCAT TGAATCTCCA GGGTTTCCAG AGAAATATCC ACACAATCTG GACTGTACCT    840

TCACCATCCT GGCCAAACCC AGGATGGAGA TCATCCTACA GTTCCTGACC TTTGACCTGG    900

AGCATGACCC TCTACAAGTG GGGGAAGGAG ACTGTAAATA TGACTGGCTG GACATCTGGG    960

ATGGCATTCC ACATGTTGGG CCTCTGATTG CAAGTACTG TGGGACGAAA ACACCCTCCA   1020

AACTCCGCTC GTCCACAGGG ATCCTCTCCC TGACCTTTCA CACCGACATG GCCGTGGCCA   1080

AGGATGGCTT CTCAGCACGT TACTATTTGG TCCACCAAGA ACCACCTGAG AACTTTCAGT   1140

GCAATGCCCC TCTGGGAATG GAGTCTGGCC GGATTGCTAA TGAACAGATC AGTGCCTCAT   1200

CCACCTTCTC TGATGGGAGG TGGACTCCTC AACAGAGCAG GCTCCATGGT GATGACAATG   1260

GCTGGACACC CAACGTGGAT TCCAACAAGG AGTATCTCCA GGTGGACCTG CGCTTCCTAA   1320

CCATGCTCAC AGCCATTGCA ACACAAGGAG CCATTTCCAG GGAGACCCAG AAGGGCTACT   1380

ACGTCAAATC GTACAAGCTG GAAGTCAGCA CAAACGGGGA AGATTGGATG GTCTACCGGC   1440

ATGGCAAAAA CCACAAGGTA TTCCAGGCTA ACAATGATGC CACCGAGTTG GTTCTGAACA   1500

AGCTGCACAC GCCGCTGTTG ACTCGTTTCA TCAGGATCCG CCCGCAGACG TGGCATTTGG   1560

GCATAGCCCT TCGACTGGAG CTCTTTGGTT GCCGGGTCAC AGATGCACCC TGCTCCAACA   1620

TGCTGGGAAT GCTCTCGGGC CTCATTGCTG ATACCCAGAT CTCTGCCTCC TCCACCCGAG   1680

AGTACCTCTG GAGCCCCAGT GCTGCCCGCC TGGTTAGCAG CCGCTCTGGC TGGTTCCCTC   1740

GGAACCCTCA AGCCCAGCCA GGTGAAGAAT GGCTTCAGGT GGATCTTGGG ACACCCAAGA   1800

CGGTGAAAGG CGTCATCATC CAGGGGGCCC GAGGAGGAGA CAGTATCACT GCCATGGAAG   1860
```

```
CCAGGGCATT TGTACGCAAG TTCAAAGTCT CCTACAGCCT AAATGGCAAG GACTGGGAAT    1920

ATATCCAGGA CCCCAGGACT CAGCAGCCAA AGCTGTTTGA AGGGAACATG CACTATGACA    1980

CCCCCGACAT CCGAAGGTTC GAGCCAGTTC CAGCACAGTA CGTGCGGGTA TACCCAGAGA    2040

GGTGGTCACC AGCGGGCATC GGGATGAGGC TGGAGGTCCT GGGCTGTGAC TGGACAGACT    2100

CAAAGCCCAC AGTGGAGACG CTGGGACCCA CCGTAAAGAG TGAAGAGACC ACCACCCCAT    2160

ATCCCATGGA TGAGGATGCC ACGGAGTGTG GGGAAAACTG CAGCTTTGAG GATGACAAAG    2220

ATTTGCAACT TCCTTCAGGA TTCAACTGCA ACTTTGATTT TCCTGAAGAG ACCTGTGGTT    2280

GGATGTACGA CCGTGCCAAG TGGCTGCAGA GTACCTGGAT CAGCAGTGCC AACCCTAACG    2340

ACAGAACGTT TCCAGATGAC AAGAACTTCC TGAAACTACA GAGCGACGGC GGACGAGAGG    2400

GCCAGTTTGG GCGGCTCATC AGCCCACCAG TGCACCTGCC CCGAAGCCCT GTGTGCATGG    2460

AGTTCCAATA CCAAGCCATG GGCGGCACG GGGTGGCACT GCAGGTGGTT CGGGAAGCCA    2520

GACAGGAAAG CAAACTCCTT TGGGTCATCC GCGAGGACCA GGGCAGCGAG TGGAAGCATG    2580

GACGCATTAT CCTGCCCAGC TATGACATGG AGTATCAGAT CGTATTCGAG GGAGTGATCG    2640

GGAAAGGGCG ATCCGGAGAG ATTTCCATCG ACGACATTCG GATAAGCACC GATGTCCCAC    2700

TGGAGAACTG CATGGAACCC ATCTCGGCTT TTGCAGTGGA CATCCCAGAA ATCCATGGGG    2760

GAGAGGGCTA TGAAGATGAG ATTGATGATG ACTATGAAGG AGATTGGAAC AACTCTTCCT    2820

CTACCTCAGG GGCTGGTAGT CCCTCATCTG GCAAAGAAAA GAGCTGGCTG TACACACTGG    2880

ACCCCATCCT GATCACCATC ATTGCCATGA GCTCGCTGGG TGTCCTGCTG GGGGCCACCT    2940

GTGCGGGCCT CCTCCTCTAC TGCACCTGCT CCTACTCTGG CCTGAGTTCG AGAAGCTGCA    3000

CCACACTGGA GAACTACAAC TTTGAGCTCT ACGACGGCCT CAAGCACAAG GTCAAGATCA    3060

ATCACCAGAA GTGCTGCTCG GAGGCATGAC CGATTGTGTC TGAATCGCTT CTGGCGTTTC    3120

ATTCCAGCGA GAGGGCTAG GAAGATTAC TTTTTTTTTC CTTTGGAAAC TGAATGCCAT      3180

AATCTGGATC AAACCGATCC AGAATACTGA AGGTATGGAC AGAACAGACA GGCCAGTCTA    3240

GGAGAAAGGA AGATGCAGCC GTGAAGGGGA TCATTGCCCA CAGAGGACAG TGGTGGTCAA    3300

GTTAATGCAG GAACCGGGCC CGTGTTCTCT GCCGGGACAC AGACAGGAGC GCATCTCCTC    3360

GGAGTCAACA G                                                        3371

(2) INFORMATION FOR SEQ ID NO:2:

(i) SEQUENCE CHARACTERISTICS:
        (A) LENGTH: 925 amino acids
        (B) TYPE: amino acid
        (C) STRANDEDNESS: single
        (D) TOPOLOGY: linear (xi) SEQUENCE DESCRIPTION: SEQ ID NO:2:

Met Asp Met Phe Pro Leu Thr Trp Ile Phe Leu Ala Leu Tyr Phe Ser
 1               5                  10                  15

Gly His Lys Val Arg Ser Gln Gln Asp Pro Pro Cys Gly Gly Arg Leu
            20                  25                  30

Asn Ser Lys Asp Ala Gly Tyr Ile Thr Ser Pro Gly Tyr Pro Gln Asp
        35                  40                  45

Tyr Pro Ser His Gln Asn Cys Glu Trp Val Val Tyr Ala Pro Glu Pro
    50                  55                  60

Asn Gln Lys Ile Val Leu Asn Phe Asn Pro His Phe Glu Ile Glu Lys
65                  70                  75                  80
```

```
            -continued

His Asp Cys Lys Tyr Asp Phe Ile Glu Ile Arg Asp Gly Asp Ser Glu
                85                  90                  95

Ser Ala Asp Leu Leu Gly Lys His Cys Gly Asn Ile Ala Pro Pro Thr
            100                 105                 110

Ile Ile Ser Ser Gly Ser Val Leu Tyr Ile Lys Phe Thr Ser Asp Tyr
        115                 120                 125

Ala Arg Gln Gly Ala Gly Phe Ser Leu Arg Tyr Glu Ile Phe Lys Thr
    130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Arg Met Glu Ile Ile Leu Gln Phe Leu
            180                 185                 190

Thr Phe Asp Leu Glu His Asp Pro Leu Gln Val Gly Glu Gly Asp Cys
        195                 200                 205

Lys Tyr Asp Trp Leu Asp Ile Trp Asp Gly Ile Pro His Val Gly Pro
    210                 215                 220

Leu Ile Gly Lys Tyr Cys Gly Thr Lys Thr Pro Ser Lys Leu Arg Ser
225                 230                 235                 240

Ser Thr Gly Ile Leu Ser Leu Thr Phe His Thr Asp Met Ala Val Ala
                245                 250                 255

Lys Asp Gly Phe Ser Ala Arg Tyr Tyr Leu Val His Gln Glu Pro Pro
            260                 265                 270

Glu Asn Phe Gln Cys Asn Ala Pro Leu Gly Met Glu Ser Gly Arg Ile
        275                 280                 285

Val Asn Glu Gln Ile Ser Ala Ser Ser Thr Phe Ser Asp Gly Arg Trp
    290                 295                 300

Thr Pro Gln Gln Ser Arg Leu His Gly Asp Asp Asn Gly Trp Thr Pro
305                 310                 315                 320

Asn Val Asp Ser Asn Lys Glu Tyr Leu Gln Val Asp Leu Arg Phe Leu
                325                 330                 335

Thr Met Leu Thr Ala Ile Ala Thr Gln Gly Ala Ile Ser Arg Glu Thr
            340                 345                 350

Gln Lys Gly Tyr Tyr Val Lys Ser Tyr Lys Leu Glu Val Ser Thr Asn
        355                 360                 365

Gly Glu Asp Trp Met Val Tyr Arg His Gly Lys Asn His Lys Val Phe
    370                 375                 380

Gln Ala Asn Asn Asp Ala Thr Glu Leu Val Leu Asn Lys Leu His Thr
385                 390                 395                 400

Pro Leu Leu Thr Arg Phe Ile Arg Ile Arg Pro Gln Thr Trp His Leu
                405                 410                 415

Gly Ile Ala Leu Arg Leu Glu Leu Phe Gly Cys Arg Val Thr Asp Ala
            420                 425                 430

Pro Cys Ser Asn Met Leu Gly Met Leu Ser Gly Leu Ile Ala Asp Thr
        435                 440                 445

Gln Ile Ser Ala Ser Ser Thr Arg Glu Tyr Leu Trp Ser Pro Ser Ala
    450                 455                 460

Ala Arg Leu Val Ser Ser Arg Ser Gly Trp Phe Pro Arg Asn Pro Gln
465                 470                 475                 480

Ala Gln Pro Gly Glu Glu Trp Leu Gln Val Asp Leu Gly Thr Pro Lys
                485                 490                 495

Thr Val Lys Gly Val Ile Ile Gln Gly Ala Arg Gly Gly Asp Ser Ile
```

```
                500                 505                 510
Thr Ala Met Glu Ala Arg Ala Phe Val Arg Lys Phe Lys Val Ser Tyr
            515                 520                 525
Ser Leu Asn Gly Lys Asp Trp Glu Tyr Ile Gln Asp Pro Arg Thr Gln
    530                 535                 540
Gln Pro Lys Leu Phe Glu Gly Asn Met His Tyr Asp Thr Pro Asp Ile
545                 550                 555                 560
Arg Arg Phe Glu Pro Val Pro Ala Gln Tyr Val Arg Val Tyr Pro Glu
                565                 570                 575
Arg Trp Ser Pro Ala Gly Ile Gly Met Arg Leu Glu Val Leu Gly Cys
            580                 585                 590
Asp Trp Thr Asp Ser Lys Pro Thr Val Glu Thr Leu Gly Pro Thr Val
        595                 600                 605
Lys Ser Glu Glu Thr Thr Thr Pro Tyr Pro Met Asp Glu Asp Ala Thr
    610                 615                 620
Glu Cys Gly Glu Asn Cys Ser Phe Glu Asp Asp Lys Asp Leu Gln Leu
625                 630                 635                 640
Pro Ser Gly Phe Asn Cys Asn Phe Asp Phe Pro Glu Glu Thr Cys Gly
                645                 650                 655
Trp Met Tyr Asp Arg Ala Lys Trp Leu Gln Ser Thr Trp Ile Ser Ser
            660                 665                 670
Ala Asn Pro Asn Asp Arg Thr Phe Pro Asp Asp Lys Asn Phe Leu Lys
        675                 680                 685
Leu Gln Ser Asp Gly Gly Arg Glu Gly Gln Phe Gly Arg Leu Ile Ser
    690                 695                 700
Pro Pro Val His Leu Pro Arg Ser Pro Val Cys Met Glu Phe Gln Tyr
705                 710                 715                 720
Gln Ala Met Gly Gly His Gly Val Ala Leu Gln Val Val Arg Glu Ala
                725                 730                 735
Arg Gln Glu Ser Lys Leu Leu Trp Val Ile Arg Glu Asp Gln Gly Ser
            740                 745                 750
Glu Trp Lys His Gly Arg Ile Ile Leu Pro Ser Tyr Asp Met Glu Tyr
        755                 760                 765
Gln Ile Val Phe Glu Gly Val Ile Gly Lys Gly Arg Ser Gly Glu Ile
    770                 775                 780
Ser Ile Asp Asp Ile Arg Ile Ser Thr Asp Val Pro Leu Glu Asn Cys
785                 790                 795                 800
Met Glu Pro Ile Ser Ala Phe Ala Val Asp Ile Pro Glu Ile His Gly
                805                 810                 815
Gly Glu Gly Tyr Glu Asp Glu Ile Asp Asp Tyr Glu Gly Asp Trp
            820                 825                 830
Asn Asn Ser Ser Ser Thr Ser Gly Ala Gly Ser Pro Ser Ser Gly Lys
        835                 840                 845
Glu Lys Ser Trp Leu Tyr Thr Leu Asp Pro Ile Leu Ile Thr Ile Ile
    850                 855                 860
Ala Met Ser Ser Leu Gly Val Leu Leu Gly Ala Thr Cys Ala Gly Leu
865                 870                 875                 880
Leu Leu Tyr Cys Thr Cys Ser Tyr Ser Gly Leu Ser Ser Arg Ser Cys
                885                 890                 895
Thr Thr Leu Glu Asn Tyr Asn Phe Glu Leu Tyr Asp Gly Leu Lys His
            900                 905                 910
Lys Val Lys Ile Asn His Gln Lys Cys Cys Ser Glu Ala
        915                 920                 925
```

(2) INFORMATION FOR SEQ ID NO:3:

(i) SEQUENCE CHARACTERISTICS:
        (A) LENGTH: 3471 base pairs
        (B) TYPE: nucleic acid
        (C) STRANDEDNESS: single
        (D) TOPOLOGY: linear (xi) SEQUENCE DESCRIPTION: SEQ ID NO:3:

```
GGCACGAGGA CCGGCTGAGG ATTTTATGGT TCTTAAGCGG ACTTAAGAGC GTTGTTTCGG     60
ATTGTTAAGA TTCCCGTTTG CTGGGTTTTC CTCCCTCAAT CGTGCTCTCC CGCGGCTGCC    120
TGGGGACTGG CTCGGCGAAG GAGGATGGAG AGGGGGCTGC CGTTGCTGTG CGCCACGCTC    180
GCCCTTGCCC TCGCCCTGGC GGGCGCTTTC CGCAGCGATA AATGTGGCGG GACTATAAAA    240
ATTGAAAACC CGGGGTACCT TACATCTCCC GGCTACCCTC ATTCTTACCA TCCAAGTGAG    300
AAATGTGAAT GGCTAATCCA AGCTCCGGAG CCCTACCAGA GAATCATGAT CAACTTCAAC    360
CCACATTTCG ATTTGGAGGA CAGAGACTGC AAGTATGACT ATGTGGAAGT GATCGATGGA    420
GAGAATGAAG GTGGCCGCCT GTGGGGAAAG TTCTGTGGGA AGATCGCACC TTCACCTGTG    480
GTGTCTTCAG GGCCATTTCT CTTCATCAAA TTTGTCTCTG ACTATGAGAC CCACGGGGCA    540
GGATTTTCCA TCCGCTATGA AATCTTCAAG AGAGGGCCCG AATGTTCTCA GAACTATACA    600
GCACCTACTG GAGTGATAAA GTCCCCTGGG TTCCCTGAAA ATACCCCAA CAGCTTGGAG     660
TGCACCTACA TCATCTTTGC ACCAAAGATG TCTGAGATAA TCCTAGAGTT TGAAAGTTTT    720
GACCTGGAGC AAGACTCAAA TCCTCCCGGA GGAGTGTTCT GTCGCTATGA CCGGCTGGAG    780
ATCTGGGATG GATTCCCTGA AGTTGGCCCT CACATTGGGC GTTACTGTGG GCAGAAAACT    840
CCTGGCCGGA TCCGCTCCTC TTCAGGCATT CTATCCATGG TCTTCTACAC TGACAGCGCA    900
ATAGCAAAGG AAGGTTTCTC AGCCAACTAC AGCGTGCTGC AGAGCAGCAT CTCTGAAGAT    960
TTCAAGTGTA TGGAGGCTCT GGGCATGGAA TCTGGAGAGA TCCATTCTGA CCAGATCACT   1020
GCATCTTCCC AGTATGGTAC CAACTGGTCT GTTGAGCGCT CCCGCCTGAA CTACCCTGAA   1080
AACGGGTGGA CACCAGGAGA GGACTCCTAC AGGGAGTGGA TCCAGGTGGA CTTGGGCCTC   1140
CTGCGATTCG TTACTGCTGT GGGGACACAG GGTGCCATTT CCAAGGAAAC CAAGAAGAAA   1200
TATTATGTCA AGACTTACAG AGTAGACATC AGCTCCAACG GAGAGGACTG GATCACCCTG   1260
AAGGAGGGAA ATAAAGCCAT TATCTTTCAG GGAAACACCA ATCCCACGGA TGTTGTCTTT   1320
GGAGTTTTCC CCAAACCACT GATAACTCGA TTTGTCCGAA TCAAACCTGC ATCCTGGGAA   1380
ACTGGAATAT CTATGAGATT TGAAGTTTAT GGCTGCAAGA TAACAGATTA CCCTTGCTCT   1440
GGAATGTTGG GCATGGTGTC TGGACTTATT TCAGACTCCC AGATTACAGC ATCCAACCAA   1500
GGAGACAGGA ACTGGATGCC AGAAAACATC CGCCTGGTGA CCAGTCGAAC CGGCTGGGCC   1560
CTGCCACCCT CACCCCACCC ATACATCAAT GAATGGCTCC AAGTGGACCT GGGAGATGAG   1620
AAGATAGTAA GAGGTGTCAT CATTCAAGGT GGGAAGCACC GAGAAAACAA AGTGTTCATG   1680
AGGAAGTTCA AGATCGCCTA CAGTAACAAT GGTTCTGACT GGAAAATGAT CATGGATGAC   1740
AGCAAGCGCA AGGCTAAGTC TTTTGAAGGC AACAACAACT ATGACACACC TGAGCTCCGG   1800
GCCTTTACAC CTCTCTCCAC AAGATTCATC AGGATCTACC CGAGAGAGC CACACATAGT    1860
GGGCTCGGAC TGAGGATGGA GCTACTGGGC TGTGAAGTAG AAGTGCCTAC AGCTGGACCC   1920
ACGACACCCA ATGGGAACCC CGTGGACGAG TGTGACGATG ACCAGGCCAA CTGCCACAGT   1980
GGCACAGGTG ATGACTTCCA GCTCACAGGA GGCACCACTG TCCTGGCCAC AGAGAAGCCA   2040
```

-continued

```
ACCATTATAG ACAGCACCAT CCAATCAGAG TTCCCGACAT ACGGTTTTAA CTGCGAGTTT    2100

GGCTGGGGCT CTCACAAGAC ATTCTGCCAC TGGGAACATG ACAGCCACGC GCAGCTCAGG    2160

TGGAGGGTGC TGACCAGCAA GACGGGGCCC ATTCAGGACC ACACAGGAGA TGGCAACTTC    2220

ATCTATTCCC AAGCTGATGA AAATCAGAAA GGCAAAGTAG CCCGCCTGGT GAGCCCTGTG    2280

GTCTATTCCC AGAGTTCTGC CCACTGCATG ACCTTCTGGT ATCACATGTC CGGCTCTCAT    2340

GTGGGTACAC TGAGGGTCAA ACTGCACTAC CAGAAGCCAG AGGAATATGA TCAACTGGTC    2400

TGGATGGTGG TCGGGCACCA AGGAGACCAC TGGAAGGAAG GGCGTGTCTT GCTGCACAAA    2460

TCTCTGAAAC TGTATCAGGT TATTTTTGAA GGTGAAATCG GAAAAGGAAA CCTCGGTGGG    2520

ATTGCTGTGG ATGATATCAG TATTAACAAC CACATTCCTC AGGAGGACTG TGCAAAACCA    2580

ACAGACCTAG ATAAAAAGAA CACAGAAATT AAAATAGATG AAACAGGGAG CACCCCAGGA    2640

TATGAAGAAG GGAAAGGCGA CAAGAACATC TCCAGGAAGC CAGGCAATGT GCTTAAGACC    2700

CTGGACCCCA TCCTGATCAC CATCATAGCC ATGAGTGCCC TGGGGGTGCT CCTGGGTGCA    2760

GTCTGTGGAG TTGTGCTGTA CTGTGCCTGT TGGCACAATG GGATGTCGGA AGGAACCTA    2820

TCTGCCCTGG AGAACTATAA CTTTGAACTT GTGGATGGTG TAAAGTTGAA AAAAGATAAA    2880

CTGAACCCAC AGAGTAATTA CTCAGAGGCG TGAAGGCACG GAGCTGGAGG GAACAAGGGA    2940

GGAGCGCGGC AGGAGAACAG TGGAGGCGCA GGGACTCTGT TACTCTGCTT TCACTGTAAG    3000

CTGGGAAGGG CGGGGACTCT GTTACTCCGC TTTCACTGTA AGCTCGGAAG GGCATCCGCG    3060

ATGCCATGCC AGGCTTTTCT CAGGAGCTTC AATGAGCATC ACCTACAGAC ACAAGCAGGT    3120

GACTGCGGTA ACAACAGGAA TCATGTACAG CCTGCTTTCT TCTCTTGGTT TCGTTTGGGT    3180

AATCAGAAGC CAGTTGAGAC CAAGTGTGAC TGACTTCATG GTTCATCCTA CTTGGCCCCC    3240

TTTTTCCTCT CTTTCTCCTT ACCCTGTGGT GGATTCTTCT CGGAAACTGC AAAATCCAAG    3300

ATGCTGGCAC TAGGCGTTGT TCAGTGGGCT CTTTCGATGG ACATGTGACC TATAGCCCAG    3360

TGCCTAGAGC ATATTAGCAT AACCACATTT CAGGGACACA CAATGTCCGC TTTTGCATCG    3420

CTACGTGCAG CGAGCACAGG AAAAAGAAAA AAAAAAAAA  AAAAACTCGA G             3471
```

(2) INFORMATION FOR SEQ ID NO:4:

(i) SEQUENCE CHARACTERISTICS:
        (A) LENGTH: 922 amino acids
        (B) TYPE: amino acid
        (C) STRANDEDNESS: single
        (D) TOPOLOGY: linear (xi) SEQUENCE DESCRIPTION: SEQ ID NO:4:

```
Met Glu Arg Gly Leu Pro Leu Leu Cys Ala Thr Leu Ala Leu Ala Leu
 1               5                  10                  15

Ala Leu Ala Gly Ala Phe Arg Ser Asp Lys Cys Gly Thr Ile Lys
                20                  25                  30

Ile Glu Asn Pro Gly Tyr Leu Thr Ser Pro Gly Tyr Pro His Ser Tyr
            35                  40                  45

His Pro Ser Glu Lys Cys Glu Trp Leu Ile Gln Ala Pro Glu Pro Tyr
        50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Ile Asp Gly Glu Asn Glu Gly
                85                  90                  95

Gly Arg Leu Trp Gly Lys Phe Cys Gly Lys Ile Ala Pro Ser Pro Val
```

-continued

```
                100                 105                 110
Val Ser Ser Gly Pro Phe Leu Phe Ile Lys Phe Val Ser Asp Tyr Glu
            115                 120                 125
Thr His Gly Ala Gly Phe Ser Ile Arg Tyr Glu Ile Phe Lys Arg Gly
        130                 135                 140
Pro Glu Cys Ser Gln Asn Tyr Thr Ala Pro Thr Gly Val Ile Lys Ser
145                 150                 155                 160
Pro Gly Phe Pro Glu Lys Tyr Pro Asn Ser Leu Glu Cys Thr Tyr Ile
                165                 170                 175
Ile Phe Ala Pro Lys Met Ser Glu Ile Ile Leu Glu Phe Glu Ser Phe
            180                 185                 190
Asp Leu Glu Gln Asp Ser Asn Pro Pro Gly Gly Val Phe Cys Arg Tyr
        195                 200                 205
Asp Arg Leu Glu Ile Trp Asp Gly Phe Pro Glu Val Gly Pro His Ile
    210                 215                 220
Gly Arg Tyr Cys Gly Gln Lys Thr Pro Gly Arg Ile Arg Ser Ser Ser
225                 230                 235                 240
Gly Ile Leu Ser Met Val Phe Tyr Thr Asp Ser Ala Ile Ala Lys Glu
                245                 250                 255
Gly Phe Ser Ala Asn Tyr Ser Val Leu Gln Ser Ser Ile Ser Glu Asp
            260                 265                 270
Phe Lys Cys Met Glu Ala Leu Gly Met Glu Ser Gly Glu Ile His Ser
        275                 280                 285
Asp Gln Ile Thr Ala Ser Ser Gln Tyr Gly Thr Asn Trp Ser Val Glu
    290                 295                 300
Arg Ser Arg Leu Asn Tyr Pro Glu Asn Gly Trp Thr Pro Gly Glu Asp
305                 310                 315                 320
Ser Tyr Arg Glu Trp Ile Gln Val Asp Leu Gly Leu Leu Arg Phe Val
                325                 330                 335
Thr Ala Val Gly Thr Gln Gly Ala Ile Ser Lys Glu Thr Lys Lys Lys
            340                 345                 350
Tyr Tyr Val Lys Thr Tyr Arg Val Asp Ile Ser Ser Asn Gly Glu Asp
        355                 360                 365
Trp Ile Thr Leu Lys Glu Gly Asn Lys Ala Ile Ile Phe Gln Gly Asn
    370                 375                 380
Thr Asn Pro Thr Asp Val Val Phe Gly Val Phe Pro Lys Pro Leu Ile
385                 390                 395                 400
Thr Arg Phe Val Arg Ile Lys Pro Ala Ser Trp Glu Thr Gly Ile Ser
                405                 410                 415
Met Arg Phe Glu Val Tyr Gly Cys Lys Ile Thr Asp Tyr Pro Cys Ser
            420                 425                 430
Gly Met Leu Gly Met Val Ser Gly Leu Ile Ser Asp Ser Gln Ile Thr
        435                 440                 445
Ala Ser Asn Gln Gly Asp Arg Asn Trp Met Pro Glu Asn Ile Arg Leu
    450                 455                 460
Val Thr Ser Arg Thr Gly Trp Ala Leu Pro Pro Ser Pro His Pro Tyr
465                 470                 475                 480
Ile Asn Glu Trp Leu Gln Val Asp Leu Gly Asp Glu Lys Ile Val Arg
                485                 490                 495
Gly Val Ile Ile Gln Gly Gly Lys His Arg Glu Asn Lys Val Phe Met
            500                 505                 510
Arg Lys Phe Lys Ile Ala Tyr Ser Asn Asn Gly Ser Asp Trp Lys Met
        515                 520                 525
```

```
Ile Met Asp Asp Ser Lys Arg Lys Ala Lys Ser Phe Glu Gly Asn Asn
    530                 535                 540

Asn Tyr Asp Thr Pro Glu Leu Arg Ala Phe Thr Pro Leu Ser Thr Arg
545                 550                 555                 560

Phe Ile Arg Ile Tyr Pro Glu Arg Ala Thr His Ser Gly Leu Gly Leu
            565                 570                 575

Arg Met Glu Leu Leu Gly Cys Glu Val Pro Thr Ala Gly Pro
        580                 585                 590

Thr Thr Pro Asn Gly Asn Pro Val Asp Glu Cys Asp Asp Gln Ala
        595                 600                 605

Asn Cys His Ser Gly Thr Gly Asp Asp Phe Gln Leu Thr Gly Gly Thr
    610                 615                 620

Thr Val Leu Ala Thr Glu Lys Pro Thr Ile Ile Asp Ser Thr Ile Gln
625                 630                 635                 640

Ser Glu Phe Pro Thr Tyr Gly Phe Asn Cys Glu Phe Gly Trp Gly Ser
            645                 650                 655

His Lys Thr Phe Cys His Trp Glu His Asp Ser His Ala Gln Leu Arg
            660                 665                 670

Trp Arg Val Leu Thr Ser Lys Thr Gly Pro Ile Gln Asp His Thr Gly
        675                 680                 685

Asp Gly Asn Phe Ile Tyr Ser Gln Ala Asp Glu Asn Gln Lys Gly Lys
        690                 695                 700

Val Ala Arg Leu Val Ser Pro Val Val Tyr Ser Gln Ser Ser Ala His
705                 710                 715                 720

Cys Met Thr Phe Trp Tyr His Met Ser Gly Ser His Val Gly Thr Leu
            725                 730                 735

Arg Val Lys Leu His Tyr Gln Lys Pro Glu Glu Tyr Asp Gln Leu Val
        740                 745                 750

Trp Met Val Val Gly His Gln Gly Asp His Trp Lys Glu Gly Arg Val
        755                 760                 765

Leu Leu His Lys Ser Leu Lys Leu Tyr Gln Val Ile Phe Glu Gly Glu
    770                 775                 780

Ile Gly Lys Gly Asn Leu Gly Gly Ile Ala Val Asp Asp Ile Ser Ile
785                 790                 795                 800

Asn Asn His Ile Pro Gln Glu Asp Cys Ala Lys Pro Thr Asp Leu Asp
            805                 810                 815

Lys Lys Asn Thr Glu Ile Lys Ile Asp Glu Thr Gly Ser Thr Pro Gly
        820                 825                 830

Tyr Glu Glu Gly Lys Gly Asp Lys Asn Ile Ser Arg Lys Pro Gly Asn
        835                 840                 845

Val Leu Lys Thr Leu Asp Pro Ile Leu Ile Thr Ile Ala Met Ser
    850                 855                 860

Ala Leu Gly Val Leu Leu Gly Ala Val Cys Gly Val Val Leu Tyr Cys
865                 870                 875                 880

Ala Cys Trp His Asn Gly Met Ser Glu Arg Asn Leu Ser Ala Leu Glu
            885                 890                 895

Asn Tyr Asn Phe Glu Leu Val Asp Gly Val Lys Leu Lys Lys Asp Lys
            900                 905                 910

Leu Asn Pro Gln Ser Asn Tyr Ser Glu Ala
        915                 920
```

(2) INFORMATION FOR SEQ ID NO:5:

```
        (i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:5:

TTYGARGGNG ARATHGGNAA RGG                                             23

(2) INFORMATION FOR SEQ ID NO:6:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:6:

NAGYTCRAAR TTRATRTTYT C                                               21

(2) INFORMATION FOR SEQ ID NO:7:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:7:

Phe Glu Gly Glu Ile Gly Lys Gly
 1               5

(2) INFORMATION FOR SEQ ID NO:8:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: None (xi) SEQUENCE DESCRIPTION: SEQ ID NO:8:

Glu Asn Tyr Asn Phe Glu Leu
 1               5
```

SCREENING ASSAYS FOR THE INTERACTION OF SEMAPHORINS AND NEUROPILINS

The applicants claim the benefit of provisional application Serial No. 60/052,762, filed Jul. 17, 1997, which application is expressly incorporated herein.

TECHNICAL FIELD OF THE INVENTION

This invention is related to the field of developmental biology. In particular it is related to the area of axon guidance cues.

BACKGROUND OF THE INVENTION

The complex wiring of the adult nervous system is dependent upon the occurrence during neurodevelopment of an ordered series of axon guidance decisions that ultimately lead to the establishment of precise connections between neurons and their appropriate targets. These guidance events can act over long or short distances, and they can be either attractive or repulsive in nature (Tessier-Lavigne and Goodman, 1996). An important first step in elucidating the mechanisms by which long-distance clemotropic cues mediate axon guidance is identification of the receptors that bind these cues. Identification of two plylogenetically conserved gene families, the semaphorins and the netrins, has advanced our understanding of the cellular and molecular basis of long-range influences on axon guidance. Semaphorins and netrins function as chemotropic cues for specifac populations of neurons during development (Keynes and Cook, 1995). The netrins have been implicated in long-range attractive and repulsive guidance events in Caenorhabditis elegans (UNC-6), vertebrates (netrin-1 and netrin-2), and Drosopila (netrin-A and netrin-B) (Serafini et al., 1994; Varela-Eclavarria et al., 1997). Genetic studies in both invertebrates and vertebrates, and biochemical studies in vertebrates, show that two immunoglobulin (Ig) superfamily subgroups, one including the Deleted in Colorectal Cancer (DCC), UNC-40, and Frazzled proteins, and the other including the UNC-5, UNC5H1, UNC5H2, and RCM proteins, contain netrin receptors involved in mediating attractive and repulsive netrin functions (Tessier-Lavigne and Goodman, 1996; Ackerman et al., 1997; Fazeli et al., 1997; Leonardo et al., 1997). At present, however, semaphorin receptors have not been identified.

The semaphorins comprise a large family of both transmembrane and secreted glycoproteins, suggesting that some semaphorins act at a distance while others act locally (Kolodkin, 1996; Puschel, 1996). Semaphorpins are defined by a well-conserved extracellular semaphorin (sema) domain of approximately 500 amino acids. Secreted semaphorins contain an Ig domain that is C-terminal to the sema domain, while transmembrane semaphorins can have an Ig domain, type 1 thrombospondin repeat, or no obvious domain motif N-terminal to their transmembrane domain. Semaphorins are present in a variety of neuronal and non-neuronal tissues. Their function in neuronal growth cone guidance, however, has been addressed most extensively.

Two secreted semaphorins, vertebrate collapsin-1/Sema III/Sem D (species homologues) and Drosophia semaphorin II (D-sema II) (Matthes et al., 1995), have been shown to function selectively in repulsive growth cone guidance during development. Collapsin-1 (Coll-1) was identified in a search for growth cone collapsing factors from the membranes of adult click brain tissue (Luo et al., 1993). Acute application of recombinant Coll-1 induces the collapse of a subset of dorsal-root-ganglia (DRG) neuron growth cones at sub-nanomolar concentrations, but has no effect on chicken retinal ganglion cell growth cones. Brain-derived membrane extracts enriched for Coll-1 and immobilized to beads, however, provided sensory neurons in culture with a localized repulsive cue capable of steering growth cones away from beads rather than causing complete growth cone collapse (Fan and Raper, 1995).

Genes encoding human, rat and mouse Sema III/Sem D (referred to below as Sema III) were identified based on their similarity to other semaphorins (Giger et al., 1996; Kolodkin et al., 1993; Messersmith et al., 1995; Puschel et al., 1995). Sema III can act as a chemorepellent for NGF-dependent embryonic (E14) DRG sensory neurons. It has little effect, however, on neurotrophin-3 (NT-3)-responsive E14 DRG sensory afferents. The E14 ventral spinal cord secretes a chemorepellent activity selective for NGF-, not NT-3-, dependent E14 DRG sensory afferents (Fitzgerald et al., 1993; Messersmith et al., 1995; Puschel et al., 1996). This correlates well with the expression pattern of sema III in the ventral cord during the time of sensory afferent innervation, and the segregation of NT-3- and NGF-dependent sensory afferents, respectively, into ventral and dorsal targets in the spinal cord (Messersmith et al., 1995).

Indeed, antibody perturbation of Coll-1 at analogous stages in chick neurodevelopment supports the idea that Coll-1 is the ventral cord repellent (Shepherd et al., 1997). This is further supported by the observation that mice with a targeted deletion of the sema III gene exhibit defects in the trajectories of certain NGF-responsive sensory afferents (Behar et al., 1996). In addition, functional studies show that Sema III can act as a chemorepellent for spinal motor neurons and a subset of cranial motor neurons (Varela-Echavarria et al., 1997). Coupled with extensive analysis of sema III and Coll-1 expression (Giger et al., 1996; Shepherd et al., 1996; Wright et al., 1995), all of these data suggest that specific populations of embryonic and adult neurons require Sema III for establishment, and possibly maintenance, of their appropriate patterns of connections. The rapid response of DRG growth cones in culture to Coll-1 and Sema III, and the low concentrations of these factors needed to elicit a response, strongly suggest that a receptor-meldated signal transluction mechanism underlies the action of these proteins on the cytoskeletal reorganization events that ultimately influence growth cone guidance.

SUMMARY OF THE INVENTION

It is an object of the present invention to provide a method of monitoring the interaction of a semaphorin and a neuropilin.

It is another object of the present invention to provide an isolated and purified subgenomic nucleic acid molecule which encodes a new mammalian neuropilin.

It is an object of the present invention to provide a method of identifying axon guidance cues.

Another object of the invention is to provide a method for monitoring the interaction between a semaphorin and a neuropilin so that agonists and antagonists can be identified.

Another object of the invention is to provide a polypeptide useful for antagonizing the interaction between a semaphorin and a neuropilin.

Another object of the invention is to provide a polypeptide useful for antagonizing the interaction between a semaphorin and a neuropilin.

It is still another embodiment of the invention to provide an antibody preparation useful for isolating and detecting a neuropilin protein.

It is yet another object of the invention to provide an isolated and purified mammalian neuropilin protein.

These and other objects of the invention are achieved by one or more of the embodiments described below. In one embodiment a method of monitoring the interaction of a semaphorin and a neuropilin is provided. The method comprises the steps of:

contacting a first protein comprising an extracellular domain of a neuropilin with a second protein which comprises an extracellular domain of a semaphorin under conditions where the extracellular domain of the neuropilin binds to the extracellular domain of the semaphorin;

determining the binding of the first protein to the second protein or second protein to the first protein.

According to yet another embodiment an isolated and purified subgenomic nucleic acid molecule is provided. The molecule encodes a mammalian neuropilin-2 and has at least 90% sequence identity to SEQ ID NO: 1.

In yet another embodiment of the invention a method of identifying axon guidance cues is provided. The method comprises the steps of:

contacting a detectably labeled mammalian neuropilin protein or semaphorin-binding portion thereof with a mixture of proteins secreted by neuronal cells;

removing proteins of the mixture which do not bind to the detectably labeled mammalian neuropilin; wherein a protein of the mixture which binds to the detectably labeled mammalian neuropilin or said portion is identified as a candidate axon guidance cue.

According to another aspect of the invention a method is provided for monitoring the interaction between a semaphorin and a neuropilin. The method comprises the steps of:

contacting a fusion protein comprising a semaphorin sema or Ig basic domain with cells which express a neuropilin;

detecting the fusion protein comprising the semaphorin sema or Ig basic domain which binds to the cells.

As another aspect of the invention a method is provided for monitoring the interaction between a semaphorin and a neuropilin. The method comprises the steps of:

contacting a protein comprising a semaphorin sema or Ig basic domain with cells which express a polypeptide comprising an extracellular domain of a neuropilin;

detecting the protein comprising the semaphorin sema or Ig basic domain which binds to the cells.

As still another aspect of the invention a polypeptide portion of neuropilin useful for antagonizing the interaction between a semaphorin and a neuropilin is provided. The polypeptidecomprises the extracellular domain of a neuropilin.

In yet another embodiment of the invention an isolated dand purified protein which is neuropilin-2 is provided. The amino acid sequence of neuropilin-2 is shown in SEQ ID NO: 2. Other neuropilins having at least 90% amino acid identity with SEQ ID NO: 2 are also provided.

According to still another aspect of the invention a method of monitoring the interaction between a semaphorin and a neuropilin is provided. The method comprises the steps of:

coculturing in a matrix (a) embryonic nerve cells with (b) cells which have been transfected with an expression construct encoding a semaphorin and which express the semaphorin;

adding to the cells an inhibitor of binding of the semaphorin and the neuropilin;

determining the inhibition of embryonic nerve cell axon outgrowth adjacent to the cells which express the semaphorin in the presence and absence of inhibitor.

As another aspect of the invention a method is provided for monitoring the interaction between a semaphorin and a neuropilin. The method comprises the steps of:

culturing embryonic nerve cells under conditions in which they display growth cones;

contacting the embryonic nerve cells with a semaphorin and an anti-neuropilin antibody;

observing the effect of the antibody on the collapse of the growth cones.

Yet another aspect of the invention is provided by an antibody preparation which specifically binds to a neuropilin protein. The antibody does not specifically bind to neuropilin-1. Particular antibodies bind exclusively to the extracellular domain.

An additional embodiment of the invention is an isolated and purified mammalian neuropilin protein which comprises a signal sequence, two complement binding domains, two coagulation factor domains, a MAM domain, a transmembrane domain and a cytoplasmic domain, with the proviso that the neuropilin protein is not neuropilin-1.

The invention thus provides the art with potent modulators of nerve cell growth, immune responsiveness, and viral pathogenesis, which can be used in the treatment and diagnosis of neurological disease and neuro-regeneration, immune modulation including hypersensitivity and graft-rejection, and diagnosis and treatment of viral and oncological infection/diseases.

The neuropilins, neuropilin-encoding nucleic acids, and unique portions thereof also are useful in screening chemical libraries for regulators of semaphorin-mediated cell activity, in genetic mapping, as probes for related genes, as diagnostic reagents for genetic, neurological, immunological, and oncological disease and in the production of specific cellular and animal systems for the development of neurological, immunological, oncological and viral disease therapy.

The medical applications of such compounds, their agonists, and their antagonists are enormous and include modulating neuronal growth regenerative capacity, treating neurodegenerative disease, and mapping (e.g., diagnosing) genetic neurological defects.

BRIEF DESCRIPTION OF THE DRAWINGS

FIGS. 1A to 1F. Sema-AP binds to neuropilin. COS cells were transfected with an expression vector encoding neuropilin (FIGS. 1A–1C) or the empty vector (FIG. 1D). After two days, cells were incubated with Sema-AP (FIG. 1A) or SEAP (FIG. 1B) and then processed for alkaline phosphatase activity, or cells were fixed and subjected to immunocytochemistry using anti-neuropilin IgG (FIGS. 1C and 1D). No neuropilin immunoreactivity was detected when COS cells expressing neuropilin were incubated with pre-immune IgG. (FIG. 1E) Anti-neuropilin immunoblot analysis of whole cell extracts prepared from COS cells that were transfected with the empty expression vector (lane 1) or an expression vector encoding neuropilin (lane 2). (FIG. 1F) Sema-AP binds directly to the extracellular domain of neuropilin. Either Sema-AP or SEAP was incubated with soluble myc-tagged neuropilin extracellular domain (myc-neuropilin$^{ex}$). Then, myc-neuropilin$^{ex}$ was immunoprecipitated with an antibody directed against the myc epitope, and alkaline phosphatase activity in the immune complex was determined as described in the Examples. AP activity was measured as described in the Examples and is reported as OD$_{405}$/second. Shown are the means +/− SEM of three independent experiments. Scale bar=25 μm.

FIGS. 2A–2E. Sema-AP binding sites and neuropilin are co-expressed on growth cones and axons of Sema III-responsive neurons. Dorsal root ganglia (DRG) explants obtained from E14 rat embryos were grown in tissue culture for two days in the presence of NGF, then processed for in situ Sema-AP binling (FIGS. 2A and 2C), SEAP binding (FIGS. 2B and 2D), or immunocytochemistry with either anti-neuropilin IgG (FIG. 2E) or pre-immune IgG (FIG. 2F). Note that both Sema-AP binding activity and anti-neuropilin immunoreactivity are detected on axons and growth cones of DRG neurons.

FIGS. 3A–3B. Scatchard analyses of Sema-AP bound to COS cells expressing neuropilin and to DRG sensory neurons. Sema-AP binding analyses were performed with COS cells that were transfected with a neuropilin expression vector (FIG. 3A), or primary cultures of dissociated rat embryonic DRG neurons (FIG. 3B). Non-specific Sema-AP binding was less than 10% of total binding as measured by Sema-AP binding to untransfected COS cells. Binding characteristics for the experiments shown were as follows: COS cells expressing neuropilin had approximately 125,000 Sema-AP binding sites per cell, and the KD=1.5×10-9. Dissociated DRG neurons had approximately 20,000 Sema-AP binding sites per cell, and the KD=0.9×10-9. Similar results were seen in at least 3 independent COS cell and dissociated DRG binding experiments.

(FIGS. 4A and 4B) DRG explants were cocultured with COS cells expressing myc-Sema III and grown for 40 hrs. in the absence (FIG. 4A) or presence (FIG. 4B) of anti-neuropilin antibodies (100 μg/ml IgG fraction). (FIG. 4C) Schematic diagram depicting DRG neurons, COS cells, and parameters measured in experiments presented in (FIG. 4D). P=proximal; D=distal. (FIG. 4D) Quantitation of the effects of anti-neuropilin antibodies on the repulsive activity of Sema III. Shown are the means +/− SEM of axon outgrowth (proximal length/distal length) of DRG neurons in the coculture assay grown in the absence (−Ab) or presence (+Ab) of anti-neuropilin IgG fraction. The degree of axon outgrowth was determined in three separate experiments. Anti-neuropilin antibodies significantly inhibited the repulsive activity of Sema III as determined by a Students T-test (P<0.0001). The average amount of axon outgrowth on lateral sides of the explants as well as the average distance between the explants and the COS cell clumps were not different between the various groups. Although the cocultures for these experiments were grown in the presence of anti-neuropilin or in the absence of rabbit antibodies, additional experiments showed that pre-immune IgG (100 μg/ml) had no effect on the repulsive activity of Sema III (P<0.001; n=21, pre-immune IgG fraction and n=26, immune IgG fraction). (FIGS. 4E–H) Neuropilin immunoreactivity was specifically detected in neurons previously shown to express neuropilin mRNA ((Kawakami et al., 1995); FIG. 6). (FIG. 4E) Cross-section of an E14.5 rat spinal cord. Strong neuropilin immunoreactivity was found in DRG (asterisk) and their central and peripheral projections. The dorsal funiculus (DF) and motor axons that leave the ventral horn (arrow; data not shown) display strong neuropilin immunoreactivity. The sympathetic chain ganglion (SG) was stained. (FIG. 4F) No labeling was detected on parallel sections processed with the pre-immune IgG. (FIG. 4G) Parasagittal sections of the head showing strong neuropilin immunoreactivity in the sensory trigeminal ganglion fG), including the ophthalmic (arrowhead) and maxillary (arrow) branches. A corresponding section stained for neuropilin mRNA by in situ hybridization revealed very strong staining in cell bodies of the trigeminal ganglion. Scale bar=400 μm, FIGS. 4A and 4B; 300 mm, FIGS. 4E and 4F; 180 mm, FIGS. 4G and 4H.

FIGS. 5A and 5B. Comparison of the deduced amino acid sequences of rat neuropilin (SEQ ID NO:4) and Npn-2 (SEQ ID NO:2). (FIG. 5A) Putative signal sequence (dashed line), the two complement binding domains (CUB domains; between the * symbols), the two coagulation factor domains (between the # symbols), the single MAM domains (between the closed circles), and the putative transmembrane domains (solid lines) of neuropilin and neuropilin-2 are indicated. (FIG. 5B) Domain alignment and amino acid identity between rat neuropilin and rat neuropilin-2; ss=putative signal sequence; a1, a2=the complement binding domains; b1, b2=the coagulation factor domains; TM=transmembrane domain; cy=cytoplasmic domain.

(FIG. 6A) Expression of semaphorin III was restricted to the ventral spinal cord, including the basal plate neuroepithelium. (FIG. 6B) Strong expression of neuropilin was observed in DRG (asterisk), motor pools in the ventral horn, the intermedolateral column (arrowhead) and the dorsal horn. (FIG. 6C) neuropilin-2 expression was detected in motor pools, the ventral horn, intermediate zone, and two dorsally extending stripes at the lateral border of the ventricular zone (small arrow). Roof plate (RP) and floor plate (FP) displayed moderate neuropilin-2 expression. Scale bar=150 μm.

DETAILED DESCRIPTION OF THE INVENTION

Figure 4A:
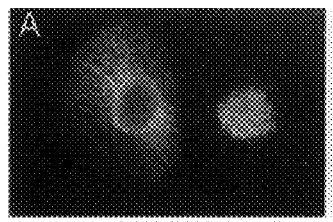
FIGS. 4A–4H. Neuropilin antibodies inhibit Sema-III-mediated repulsion of NGF-dependent DRG neurons.

We have identified a high affinity semaphorin receptor and shown it to be neuropilin, an axonal glycoprotein. Neuropilin has been characterized by Fujisawa and colleagues. Prior to its identification as a semaphorin receptor, the role played by neuropilin during development was unclear. Our finding, however, demonstrates that neuropilin mediates repulsive guidance decisions. Further, we have found that neuropilin is one of a family of proteins that is expressed differentially in the mammalian nervous system during development.

Recently it has been found that VEGF binds to neuropilin. The binding enhances the signalling achieved by VEGF binding to the KDR receptor. Among other biological effects, VEGF is involved in vascularization of tumors. It is a further discovery of the present invention that overlapping regions of neuropilin bind to semaphorin and VEGF (i.e., the B domains or the coagulation factor domains). Thus semaphorin antagonizes the binding of VEGF to neuropilin. (Similarly, VEGF antagonizes the binding of semaphorin to neuropilin.) Thus semaphorin, or another substance which has similar binding properties, can be used to inhibit vascularization of tumors, and subsequent metastasis. Such substances can be found by the methods disclosed in this application. Semaphorin, neuropilin-binding portions of it, such as the sema domain or the Ig basic domain, or other neuropilin-binding substances, can be administered to tumors by direct administration to the tumor. Alternatively, the substance may be administered systemically. The substance may be targeted, if desired to the tumor using appropriate ligands which bind to the tumor. The substance may be encapsulated in liposomes or other protective formulations. Polynucleotides encoding semaphorin or a neuropilin-binding portion of it can be delivered to the tumor to inhibit vascularization as well.

A number of methods for monitoring the interaction of a semaphorin and a neuropilin are provided. These can be used to identify agents or conditions which inhibit or enhance the interaction. Such agents may be useful as agonists or antagonists. Two proteins each having at least an extracellular domain sufficient for binding of the other protein, neuropilin and semaphorin, are contacted. The binding of the two proteins occurs in the extracellular domain portions. In particular, the binding occurs in the A and B domains of neuropilin. Either the sema domain or the Ig basic domain of semaphorin can be used to bind to neuropilin. The sema domain requires the A and B domains of neuropilin for binding. The Ig basic domain of semaphorin requires only the B domain of neuropilin to bind. Nonetheless, any portion of the binding partners which is selected from the extracellular portion of the partners and which is sufficient to effect binding with the other binding partner may be used.

After binding has occurred the binding of the two proteins to each other can be determined. For example, one of the two binding partners can be detected immunologically, enzymatically, fluorescently, or radiochemically. This is particularly convenient if one of the two partners had been affixed to a solid support prior to the step of binding. Suitable solid supports are known in the art and include microtiter dishes, column packing materials, beads, and the like. An ELISA format is particularly convenient. Binding can be determined by quantitative or qualitative methods. Either or both of the bound partners can be determined, or the amount which does not bind can be determined.

Alternatively, after binding has occurred an antibody can be used to immunoprecipitate the protein binding complex formed. The antibody may bind to either of the two binding partners as the antigen. The presence of the non-antigen binding partner is determined in the immunoprecipitate. Only if the two proteins bind will the non-antigen be found in the immunoprecipitate. The presence of the non-antigen binding partner in the immunoprecipitate can be detected by any means known in the art. These include analysis on SDS-polyacrylamide gels and immunoassay with an antibody to the opposite binding partner to that used for the immunoprecipitation. The proteins used in the method may be fusion proteins, isolated portions of the binding partners, or the full-length binding partners. As each of semaphorin and neuropiln define gene families, any semaphorin and any neuropilin may be used as binding partners. The proteins may desirably lack a transmembrane and an intracellular domain. One of the two proteins may be "tagged" with an unrelated protein sequence, for easy manipulation and recognition. For example, myc sequences can be covalently appended to the binding partner, preferably by genetic engineering, to form a binding partner which can be detected and/or purified using an anti-myc antibody. Fusion proteins may conveniently comprise a second protein which has a desirable feature or biological activity, such as an enzymatic activity, or a binding activity. One such fusion protein which has been particularly useful contains alkaline phosphatase, which produces a colored product upon conversion of a suitable substrate, such as NBT and BCIP. Other such enzymes as are known in the art can readily be used.

Test compounds can be added to one or both of the binding partners in the binding reaction, either before, during, or after the binding reaction. The effect of a test compound on the binding reaction can be used to identify agents useful as agonists or antagonists.

Another variation on the monitoring of the binding interaction involves the use of cells which express a neuropilin. Cells can be tested for expression of a neuropilin using antibodies or any other means known in the art. Cells which have been transfected with a gene construct such that they express a neuropilin can also be used. Using such transfectants, one is not limited to use of cells which naturally express neuropilns. Moreover, using such constructs, one has an excellent null-binding control in the non-transfected cells. Since the neuropilins are expressed on the surface of cells, there is no need to lyse or otherwise treat or permeabilize the cells prior to binding. In this variation, use of a fusion protein comprising an enzyme and a semaphorin is particularly convenient. See examples, below.

Another variation on the method used to monitor the binding interaction of semaphorins and neuroplins is a two-cell assay. In such an assay two cell types are co-cultured in a matrix which limits diffusion of secreted products. Suitable matrices for growth of cells are known in the art and include collagen matrices. DRG cells can be used as the neuropilin expressing cells. The semaphorin-secreting cells can be cells transfected with a semaphorin expression construct. An inhibitor of the binding interaction is added to the culture and the inhibition of axon outgrowth adjacent to the semaphorin-secreting cell is determined. Outgrowth of axons can be observed under a microscope directly or can be immunostained prior to observation to enhance visibility of axon processes. One inhibitor which can be used is an anti-neuropilin antibody. Anti-(MAM and B) domain antibodies have been found to function as such an inhibitor. Other inhibitors which can be used include polypeptides which comprise an extracellular domain of a neuropilin, preferably comprising a B domain and/or an A domain. Testing the ability of test compounds to affect the binding interaction is also contemplated. Such testing may identify useful agonists and antagonists of axon guidance cuing.

Another method of monitoring the interaction of a neuropilin and a semaphorin is by observing the effect of a semaphorin on growth cones of cultured embryonic neuronal cells, such as DRG cells. Inhibitors of the interaction of neuropilins and semaphorins can be added and their effects on the collapse of growth cones observed. Suitable inhibitors include anti-neuropilin antibodies, anti-B domain antibodies, polypeptides consisting of an extracellular domain of neuropilin. Others may be used as become known. Test compounds can also be added to determine their agonistic or antagonistic capabilities.

According to yet another method of the invention test compounds can be tested to determine if they enhance or decrease the binding of semaphorin to neuropilin. Due to the overlapping binding region of VEGF and semaphorin on neuropilin, compounds which influence semaphorin binding to neuropilin will also influence VEGF binding. This assay can use whole binding partners or polypeptides comprising binding-sufficient portions.

Axon guidance cues can be identified using the systems disclosed here. A mammalian neuropilin protein, or semaphorin binding portion thereof, can be used as a probe to detect other axon guidance cues. These may include other members of the semaphorin family or other axon guidance cues having other effects. Preferably the neuropilin protein is detectably labeled. A mixture of proteins is contacted with the neuropiln protein and non-bound proteins are removed, for example by washing, rinsing, and the like. A protein which is found to bind to the neuropilin is identified as a candidate axon guidance cue.

It has been found that neuropilin (as described by Kitsukawa et al.) is a member of a gene family having multiple members. Neuropilin is therefore now called neuropilin-1. A second member of the family is neuropilin-2. This protein is 44% identical overall to neuropilin-1. (See FIG. 5.) However, it shows remarkable conservation of its domain structure. Each neuropilin has two complement binding domains (see Bork & Beckman, 1993, *J.Mol. Biol.* 231:539–545), two coagulation factor domains (Toole et al. 1984, *Nature* 312:342–347; Jenny et al. 1987, *Proc. Natl., Acad. Sci. USA* 84:4846–4850; Sanchez, M. et al. (1994) *Proc. Natl. Acad. Sci.* 91:1819–1823; Larocca et al.(1991) *Cancer Res.* 51:4994–4998), a MAM domain (Beckman & Bork, 1993 *Trends Biochem. Sci.* 18:40–41), a single transmembrane domain, and a strikingly short cytoplasmic domain. A subgenomic nucleic acid molecule which encodes neuropilin-2 is provided. The nucleic acid molecule is smaller than the whole chromosome on which the gene naturally resides in vivo. The nucleic acid may be purified RNA or purified genomic DNA or cDNA. Other neuropilin-2 molecules which share at least 75%, 80%, 85%, 90%, or even 95% identity with the amino acid sequence or the nucleotide sequence disclosed for rat neuropilin-2 are also contemplated. These can be obtained, as is known in the art, using such techniques as RT-PCR and degenerate oligonucleotide probe hybridization. The rat and mouse neuropilin-1 molecules are about 98% identical and human neuropilin-1 is about 92% identical to the rat and mouse proteins. Other neuropilin protein molecules can be obtained functionally, as discussed in the examples, by isolating expression clones which bind to semaphorins.

Also useful are portions of the neuropilin proteins. These can be used to antagonize the interaction between a semaphorin and a neuropilin. The whole extracellular domain of a neuropilin protein can be used or one or more domains of the whole extracellular domain can be used. Suitable domains include the complement binding domains, the coagulation factor domains, and the MAM domain. These may be useful as immunogens for generating inhibitory antibodies. The A and B domain of neuropilin, i.e., the coagulation factor domain, may be useful as a semaphorin (ligand) binding site. Use of the ligand binding site may inhibit semaphorin's biological effects by titrating semaphorin away from the neuropilins which are on the neurons. B (coagulation factor) domains of other non-neuropilins may be useful for this purpose as well.

Antibodies which specifically bind to a neuropilin protein are also useful for inhibition of the neuropilin-semaphorin binding reaction. Polypeptide portions of the neuropilins can be used as immunogens to raise such antibodies. They may be polyclonal or monoclonal. Techniques for raising such antibodies are well known in the art. Antibodies such as those disclosed below which were raised against the MAM and B domain and which inhibit the biological effect of semaphorins on axonal growth and/or orientation are desirable.

In addition to neuropilin-derived polypeptides and peptides, other prospective agents are screened from large libraries of synthetic or natural compounds. For example, numerous means are available for random and directed synthesis of saccharide, peptide, and nucleic acid based compounds. Alternatively, libraries of natural compounds in the form of bacterial, fungal, plant and animal extracts are available or readily producible. Additionally, natural and synthetically produced libraries and compounds are readily modified through conventional chemical, physical, and biochemical means. See, e.g., Houghten et al. and Lam et al (1991) *Nature* 354, 84 and 81, respectively and Blake and Litzi-Davis (1992), *Bioconjugate Chem* 3, 510.

The subject peptides/polypeptides are isolated, meaning unaccompanied by at least some of the material with which they are associated in their natural state. Generally, an isolated polypeptide constitutes at least about 1%, preferably at least about 10%, and more preferably at least about 50% by weight of the total protein in a given sample. "Pure polypeptide" is intended to mean at least about 90%, preferably at least 95%, and more preferably at least about 99% by weight of total protein. Included in the subject polypeptide weight are any atoms, molecules, groups, or polymers covalently coupled to the subject neuropilin/receptor polypeptide, especially peptides, proteins, detectable labels, glycosylations, phosphorylations, etc.

The subject polypeptides may be isolated or purified in a variety of ways known to those skilled in the art depending on what other components are present in the sample and to what, if anything, the polypeptide is covalently linked. Purification methods include electrophoretic, molecular, immunological and chromatographic techniques, especially affinity chromatography and RP-HPLC in the case of peptides. For general guidance in suitable purification techniques, see Scopes, R., *Protein Purification*, Springer-Verlag, N.Y. (1982).

The subject polypeptides generally comprise naturally occurring L-amino acids but D-amino acids or amino acid mimetics coupled by peptide bonds or peptide bond mimetics may also be used. Amino acid mimetics are other than naturally occurring amino acids that conformationally mimic the amino acid for the purpose of the requisite neuropilin/receptor binding specificity. Suitable mimetics are known to those of ordinary skill in the art and include beta—gamma, and delta amino—and imino acids, cyclohexylalanine, adamantylacetic acid, etc., modifications of the amide nitrogen, the alpha-carbon, amide carbonyl, backbone modifications, etc. See, generally, Morgan and Gainor (1989) *Ann. Repts. Med. Chem* 24, 243–252; Spatola (1983) *Chemistry and Biochemistry of Amino Acids, Peptides and Proteins*, Vol VII (Weinstein) and Cho et. al (1993) *Science* 261, 1303–1305 for the synthesis and screening of oligocarbamates.

The subject neuropilin polypeptides preferably have a "semaphorin-binding specificity" meaning that the subject polypeptide retains a molecular conformation specific to one or more of the disclosed neuropilins and specifically recognizable by a semaphorin, anti-neuropilin antibody, etc.

"Specific binding" is empirically determined by contacting, for example, a neuropilin-derived peptide with a mixture of components and identifying those components that preferentially bind the neuropilin. Specific binding is most conveniently shown by competition with labeled ligand using recombinant neuropilin peptide either in vitro or in cellular expression systems as disclosed herein. Generally, specific binding of the subject neuropilin has binding affinity of $10^{6-}$M, preferably $10^{-8}$ M, more preferably $10^{-10}$ M, under in vitro conditions as exemplified below.

The polypeptides may be modified or joined to other compounds using physical, chemical, and molecular techniques disclosed or cited herein or otherwise known to those skilled in the relevant art to affect their semaphorin-binding specificity or other properties such as solubility, membrane transportability, stability, binding specificity and affinity, chemical reactivity, toxicity, bioavailability, localization, detectability, in vivo half-life, etc. as assayed by methods disclosed herein or otherwise known to those of ordinary skill in the art.

Neuropilin-1 is Expressed and Functions in Sema-III-responsive Tissues

Neuropilin (previously known as A5) was first identified as a membrane-associated glycoprotein expressed in the tectum of *Xenopus laevis* (Takagi et al., 1987). More recent analyses have demonstrated that mammalian, Xenopus, and avian neuropilin are present in a number of discrete neuronal populations (Kawakami et al., 1995; Satoda et al., 1995; Takagi et al., 1995). Importantly, neuropilin distribution patterns in the developing mouse nervous system support our conclusion that it is a Sema III receptor. During mouse development, neuropilin is present in several populations of neurons known to be responsive to Sema III, including DRG sensory neurons, post-ganglionic sympathetic neurons, trigeminal motor neurons, and spinal motor neurons (Kawalami et al., 1995; Messersmith et al., 1995; Puschel et al., 1995; Puschel et al., 1996; Shepherd et al., 1996; Takagi et al., 1991; Takagi et al., 1995; Takagi et al., 1987; Varela-Echavarria et al., 1997). Neuropilin is also expressed in many other populations of developing neurons whose ability to respond to Sema III has yet to be determined. These include several cranial nerve sensory ganglia, primary olfactory neurons, and neurons within the lippocampus and neocortex.

In addition to biochemical evidence and expression patterns, genetic evidence also suggests that neuropilin is a receptor for Sema III in vivo. Transgenic mice that overexpress neuropilin and mutant mice with a targeted deletion of the sema III gene have remarkably similar phenotypes, indicating that both neuropilin and sema III are likely to contribute to the morphogenesis of a similar, if not identical, set of tissues (Belar et al., 1996; Kitsukzawa et al., 1995). In the nervous system, loss of sema III function and overexpression of neuropilin produce defects in DRG sensory afferent projections in the spinal cord. In addition, neuropilin overexpression results in defasciculation and ectopic sprouting of spinal motor nerves in regions where non-neuronal Sema III is likely to function as a guidance cue (Giger et al., 1996; Wright et al., 1995). Further, sema III mutant and neuropilin overexpressing mice have simliar cardiovascular and bone defects. For example, both mutants have grossly abnormal hearts with dilated, thin-walled, right atria. Moreover, the sema III mutant mice and neuropilin overexpressing mice both exhibit improper skeletal development. These phenotypes, coupled with the expression of neuropilin and sema III in these tissues (Giger et al., 1996; Kawakami et al., 1995; Kitsukawa et al., 1995; Wright et al., 1995), suggest that both gene products function in a common signaling pathway. In addition to providing indirect, yet compelling, support for our conclusion that neuropilin is a receptor for Sema III in vivo, these data show that Sema III and neuropilin influence development of both neuronal and non-neuronal cells.

Neuropilins and Semaphorin Signaling

Secreted and transmembrane semaphorins are likely to affect neurodevelopment, at least in part, through their influence on repulsive growth cone steering decisions (secreted semaphorins: as described above; transmembrane semaphorins: H.-H. Yu., H. Araj, S. Ralls, and A. K., in preparation). In vitro, application of Coll-1 to NGF-dependent DRG neurons induces collapse of their growth cones, and this event is mediated by changes associated with the actin cytoskeleton within the growth cone. Growth cones exposed to Coll-1-enriched membrane extracts undergo a loss of F-actin at their leading edges relative to their centers that is not accompanied by alterations in intracellular $Ca^{2+}$ levels (Fan et al., 1993; Ivains et al., 1991). Coll-1 induced growth cone collapse is pertussis toxin (PTX) sensitive, though at present it is unclear whether this effect is directly mediated by ADP ribosylation of G proteins (Goshima et al., 1995; Kindt and Lander, 1995). Our finding that neuropilin is a Sema III receptor suggests that Sema III intracellular signaling does not proceed directly though a G protein-coupled mechanism. A gene encoding collapsin response mediator protein (CRMP-62) was cloned using this strategy and found to be necessary both for mediation of Coll-1-induced inward ion currents in oocytes and for the activity of Coll-1 on DRG neurons (Goshima et al., 1995). CRMP-62 is a member of a family of related intracellular proteins that includes four members variously expressed in the developing and adult rat nervous system, and also the *C. elegans* protein UNC-33 protein, which is required for axonal elongation and fasciculation (McIntire et al., 1992; Wang and Strittmatter, 1996). The mechanism by which CRMP-62 mediates Coll-1 or Sema III effects on DRG growth cones is unknown.

Neuropilin binds Sema III in the extracellular environment of Sema III-responsive growth cones, and it participates, possibly directly, in propagation of the Sema III signal to the intracellular components that influence actin-based changes in growth cone morphology. The extracellular portions of neuropilin and neuropilin-2 consist of three motifs found in other transmembrane proteins: the complement binding domains (CUB), the coagulation factor domains, and the MAM domains. One or all of these domains may be important for semaphorin binding or for other neuropilin functions (Hirata et al., 1993; Takagi et al., 1995). Our finding that anti-neuropilin antibodies generated against the neuropilin (MAM and B) domain inhibited the repulsive activity of Sema III on NGF-dependent DRG neurons suggests that one of these domains participates in Sema III binding. In fact, structure-function analysis has demonstrated that the A and B domains both contribute to binding.

The mechanism by which neuropilin transmits the Sema III signal to the interior of the growth cone remains unknown. The intracellular domain of neuropilin is short and contains no motifs with obvious catalytic function nor any domains that offer clues regarding the mechanism of Sema III signal translduction. However, because the intracellular domains of neuropilin and neuropiln-2 are similar with respect to both primary sequence and length, it is likely they share a common signaling mechanism. At least two possible mechanisms of neuropilin signaling exist. Neuropilin may function alone to transduce the Sema III signal. In this model, the intracellular domain of neuropilin could have a novel mechanism of coupling extracellular cues to the inside of the cell. For example, CRMP-62 may associate directly with the intracellular domain of neuropilin, and the activity of CRMP-62 may be modulated upon Sema III binding to neuropilin. Alternatively, a distinct unidentified signaling component of a Sema III receptor complex may exist, as is the case for several other ligand/receptor systems including the CNTF receptor (Ip and Yancopoulos, 1996). In this model, neuropilin may be a ligand binding component and a distinct protein(s) may associate with neuropilin and function to transmit a biochemical signal into the cytoplasm. Future studies will provide insight into the biochemical interactions between neuropilin, CRMP-62, and other signaling molecules that influence cytoskeletal dynamics of growth cones upon encountering Sema III.

Neuropilin and Neuropilin-2 Define a Gene Family

Sema III is one member of a large family of phylogenetically conserved proteins with diverse patterns of neuronal and non-neuronal expression (Kolodkin, 1996; Pusclel, 1996). It is likely that these proteins participate in many aspects of development. Therefore, it is important to identify receptors for all of the semaphorins in order to begin to determine their mechanisms of action in target cells. Our identification of neuropilin-2 provides evidence for the existence of a family of neuropilin receptors, and for a model in which at least two neuropilin receptors mediate the cellular responses of semaphorin family ligands.

Neuropilin and neuropilin-2 are closely related proteins that share a common domain structure and a significant degree of amino acid identity throughout their entire length. The structural conservation of these proteins suggests that they share a common function. Neuropilin and neuropilin-2 display unique patterns of expression in the spinal cord, the remainder of the CNS, as well as other non-neuronal tissues. Therefore, it is likely that neuropilin and neuropilin-2 influence semaphorin-mediated guidance decisions in distinct populations of developing neurons.

The above disclosure generally describes the present invention. A more complete understanding can be obtained by reference to the following specific examples which are provided herein for purposes of illustration only, and are not intended to limit the scope of the invention.

EXAMPLE 1

Neuropilin is a Sema III Binding Protein

To identify cell surface receptors for Sema III, we used a COS cell expression cloning strategy that employed a Sema III-secreted placental alkaline phosphatase fusion protein (Sema-AP) (Flanagan and Leder, 1990). A COS cell cDNA expression library was constructed using mRNA obtained from rat E14 spinal cord and DRG. cDNAs generated from these mRNAs should encode functional Sema III receptors since Sema III as well as Sema-AP induce collapse of growth cones from NGF-responsive DR neurons. The cDNA expression library was divided into 140 pool, each containing approximately 750 clones, and cDNA from each pool was transfected into separate wells of COS cells. Two days after transfection, COS cells were fixed, incubated with a solution containing Sema-AP, washed, and then stained for alkaline phosphatase (AP) activity. One positive pool was identified by the presence of a single COS cell with Sema-AP binding activity. This positive pool of cDNAs was subdivided and re-screened several times until a single cDNA was obtained that conferred Sema-AP binding when expressed in COS cells (FIG. 1A).

Figure 4B:
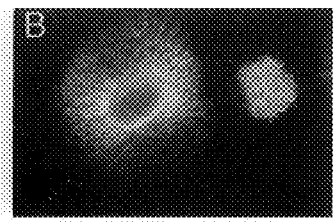
Figure 4C:
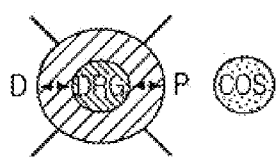
Figure 4D:
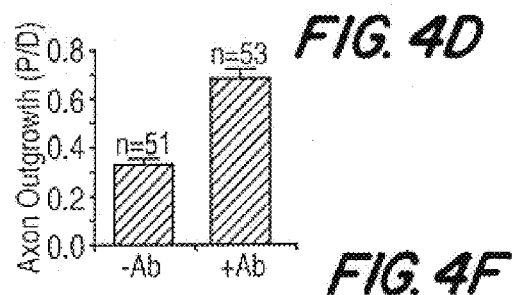
Figure 4E:
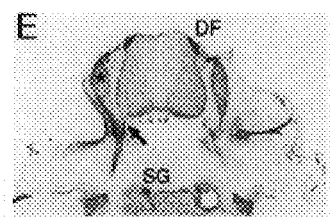
Figure 5B:
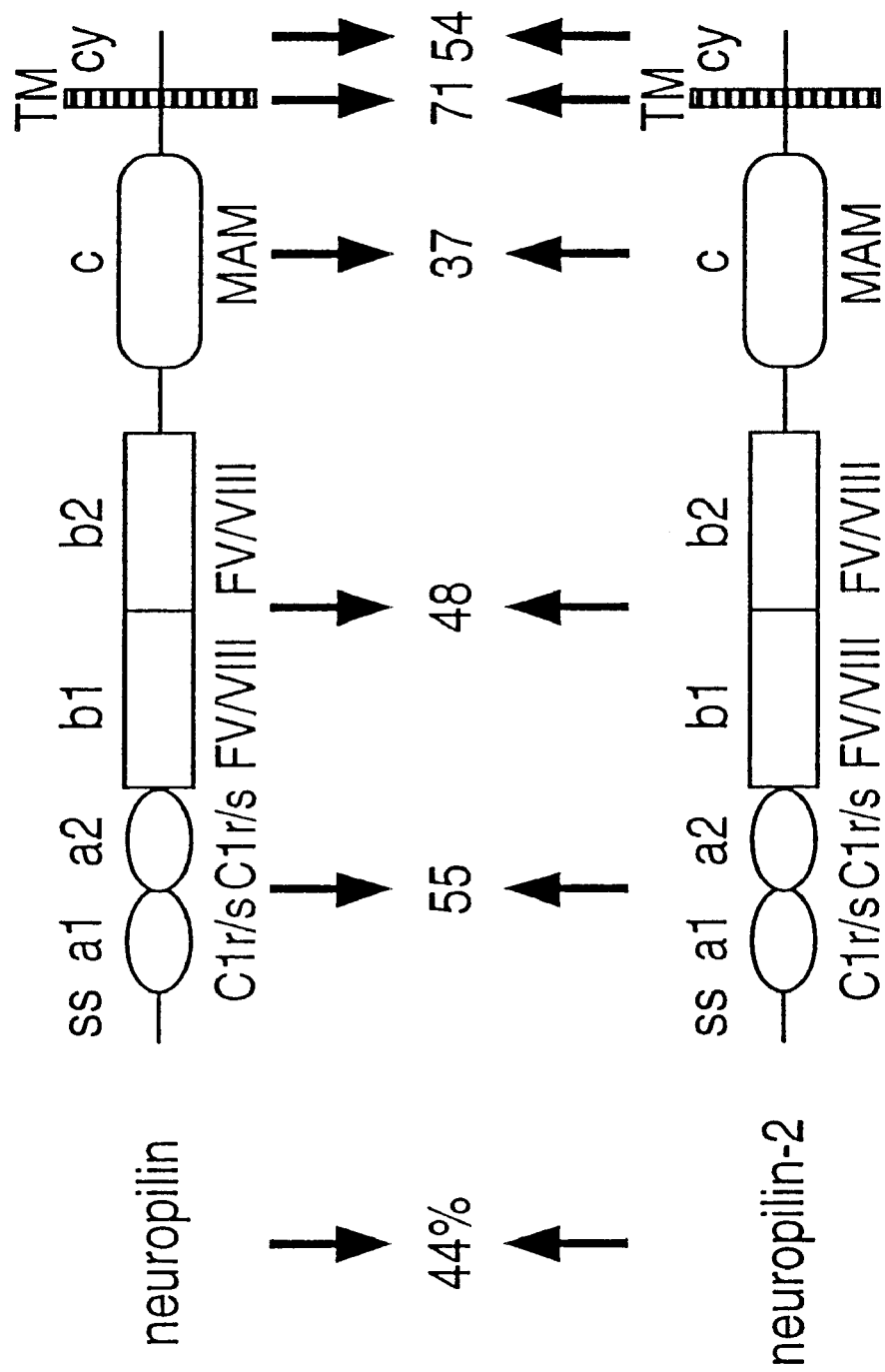

Sequence analysis revealed that the Sema-AP binding protein was the full length rat homologue of mouse neuropilin, a protein previously identified and well characterized in mice and other vertebrates (Kawakami et al., 1995). Neuropilin is a type I transmembrane protein that is expressed in a number of populations of neurons, including DRG neurons and spinal motor neurons ((Kawakami et al., 1995); FIGS. 2E, 4E). The neuropilin protein consists of a large extracellular domain, a single transmembrane domain, and a short 39 amino acid intracellular domain (FIG. 5). Sema-AP fusion protein bound to neuropilin via its Sema III domain, not the AP domain, because secreted placental alkaline phosphatase (SEAP) alone did not bind to COS cells expressing neuropilin (FIG. 1B). Moreover, Sema-AP binding to COS cells expressing neuropilin was inhibited by myc epitope-tagged Sema III (Sema-myc), and Sema-myc bound directly to COS cells expressing neuropilin but not to untransfected COS cells. Lastly, anti-neuropilin antibodies, directed against a bacterial fusion protein that included the C-terminal MAM domain as well as a portion of the B domain of neuropilin, detected neuropilin in COS cells transfected with a neuropilin expression vector, as shown by immunocytochemistry (ICC) and immunoblotting (FIGS. 1C, E). Together, these results demonstrate that Sema III binds to neuropilin that is expressed on the surface of COS cells.

While our results suggest that neuropilin is a Sema III binding protein, it remained possible that Sema-AP bound to a complex of neuropilin and an endogenous COS cell protein(s), or that neuropiln induced the expression of an endogenous Sema III binding protein in COS cells. Therefore, we next asked whether Sema-AP binds directly to neuropilin in a co-immunoprecipitation assay. For these experiments, an N-terminal myc-tagged neuropilin protein lacking the neuropilin transmembrane and intracellular domains (myc-neuropilin$^{ex}$) was used to assess whether the extracellular domain of neuropilin can directly interact with Sema III. Myc-neuropilin$^{ex}$ was expressed in COS cells and the tissue culture medium was then incubated with either Sema-AP or SEAP alone. Upon precipitation of the myc-neuropilin$^{ex}$ with a monoclonal antibody directed against the myc epitope, co-precipitation of Sema-AP was determined by the presence of AP activity in the immune complex (FIG. 1F). In contrast, no AP activity above background levels was detected in anti-myc immune complexes collected from samples in which myc-neuropilin was incubated with SEAP alone. These results demonstrate that Sema III associates directly with neuropilin.

We next compared the spatial distribution of neuropilin and Sema III binding sites present on the surface of cultured NGF-dependent DRG neurons. Sema-AP binding sites were detected all over the neurons, including their growth cones (FIGS. 2A, C). Again, SEAP alone did not bind to DRG neurons, demonstrating that Sema-AP binding was dependent on the Sema III domain, not the AP domain, of the fusion protein (FIGS. 2B, D). To assess neuropilin distribution we first subjected extracts of E14 DRG and spinal cord to immunoblotting using our anti-neuropilin antibodies described above. These antibodies detected a single ~130 kDa band which was not observed with pre-immune IgG. Using these antibodies, neuropilin immunoreactivity was seen on growth cones, axons and cell bodies of cultured DRG neurons (FIG. 2E).

Generation of Sema-AP, Myc-neuropiln

To generate the H-Sema III-alkaline phosphatase fusion protein (Sema-AP) expression vector, the human Sema III coding sequences (Kolodkin et al., 1993) were inserted into the Hind III and Bgl II sites of pAPtag-1 (Flanagan and Leder, 1990) to generate a Sema-AP fusion. Then, the entire Sema-AP sequence was excised from the pAPtag-1 vector and inserted into the Hind III and Xho I sites of pCEP4, an expression vector designed to provide high level expression in the EBNA subclone of 293 cells (Invitrogen). Myc epitope-tagged, secreted neuropilin (myc-neuropilin$^{ex}$) expression construct was generated as follows: A 2.5 kb fragment of neuropilin lacking the coding determinants of the transmembrane and intracellular domains was obtained by PCR using the entire neuropilin ORF sequence in pcDNA3 (Invitrogen) as a template. The PCR fragment was digested with EcoRI and Xba I and subcloned into a pBluescript vector containing a Kozak consensus sequence, myc epitope tag, and signal sequence originating from peptidylglycine alpha-amidating monooxygenase (PAM) (a gift of Richard Mains and Ruth Marx). This plasmid was digested with Not I, Sal I, and Sca I, and a fragment encoding the Kozak consensus sequence, PAM signal sequence, myc epitope tag, and the entire extracellular domain of neuropilin was isolated. This fragment was then cloned into the Not I and Sal I sites of the pCIneo mammalian expression vector (Promega).

Expression Library Construction and Screening

Polyadenylated RNA isolated from embryonic day 14 rat spinal cord and associated dorsal root ganglia was used to generate cDNA (ZAP-cDNA synthesis Kit; Stratagene). Subsequently, the cDNA was size fractionated and cDNA within fractions containing the largest fragments was ligated into the pMT21 COS cell expression vector (a modified version of pMT2 (Sambrook et al., 1989; Serafni et al., 1994). The ligation products were transformed into E. Coli (ElectroMAX DH10B; Gibco/BRL), and approximately 750 bacterial colonies were grown on 140 separate plates and harvested to generate 140 pools of cDNAs. Plasmid DNA was isolated from each pool using the Wizard DNA purification system (Promega) and, then, each cDNA pool was independently transfected into COS cells (1×105 cells per 35 mm well of cells) using a Lipofectamine-mediated DNA transfection procedure (Gibco/BRL). Two days after transfection, cells were incubated with Sema-AP, and bound Sema-AP was visualized following an alkaline phosphatase assay done essentially as described (Flanagan and Leder, 1990). Several pools containing one or more plasmids capable of conferring Sema III-AP binding activity were identified, and these pools were used to generate successively smaller plasmid pools followed by transfection and Sema III-AP binding assays. Ultimately, transfection of a single cDNA clone conferred Sema-AP binding activity in transfected COS cells. This clone, encoding rat neuropilin, was sequenced on both strands using the fluorescent di-deoxy terminator method of cycle sequencing on a Perkin elmer Applied Biosystems Division 373a automated DNA sequencer.

Co-precipitation of Sema-AP and the Secreted, Extracellular Domain of Neuropilin COS cell supernatant containing myc-neuropilin$^{ex}$, 293 EBNA cell supernatant containing SEAP, or 293 EBNA cell supernatant containing Sema-AP was filter-sterilized and concentrated. Samples containing equal amounts of control supernatants or supernatants containing myc-neuropilin$^{ex}$ were mixed with samples containing either Sema-AP or SEAP (equal amounts of AP activity). These mixtures were incubated at room temperature for 2 hours. Then, an equal volume of an immunoprecipitation buffer (20 mM Tris, pH 8.0, 140 mM NaCl, 0.5 mM EDTA and 2% Np-40) was added to each mixture, and the samples were centrifuged at 15,000×g for 15 minutes at 4° C. Supernatants were recovered, and 4 ml of anti-myc antibody (antibody 9E10 ascites fluid) was added to each and samples were incubated with mixing at 4° C. for 2 hours. Then, 50 ml of protein G sepharose was added to each tube, and immune complexes were collected after one hour. Immune complexes were washed three times with immunoprecipitation buffer, once with PBS, and then the immune complexes were resuspended in PBS. Liquid alkaline phosphatase assays were performed as described above. Background was defined as the amount of AP activity detected in samples in which myc-tagged myc-neuropilin$^{ex}$ was omitted from the sample incubations, and this value was subtracted from all other measurements.

Neuropilin Antisera Production and Immunoblot Analysis

Anti-neuropilin antibodies were produced by immunizing rabbits with a 6-histidine-tagged neuropilin protein which was produced in E. Coli. The bacterial expression construct was made by PCR-amplification of a fragment encoding amino acids 583–856 of rat neuropilin (amino acids 583–856 of SEQ ID NO:2) and inserted into the EcoRI and Hind III sites of pTrcHisA (Invitrogen). Expressed protein was purified by immobilized nickel-chelate affinity chromatography. Rabbits were immunized with 375 mg protein in complete Freunds adjuvant, and boosted every two to three weeks with 250 mg protein in incomplete Freunds adjuvant. Serum was collected and the IgG fraction was purified by Protein A Sepharose chromatography. Immunoblot analysis was performed as described (Ginty et al., 1994), using extracts of neuropilin transfected and untransfected COS cells, and E14 DRG and spinal cord.

Immunohistochemistry

E14.5 rat embryos were fixed for 4 hours in ice cold PBS containing 4% paraformaldehyde, and cryoprotected overnight in the same solution containing 15% sucrose. Immunocytochemistry of cryosections (20 μm) using either immune or preimmune rabbit anti-neuropilin, IgG fraction (0.7 μg/ml) was done as described (Giger et al., 1996).

EXAMPLE 2

Sema III Binds to Neuropilin with High Affinity

Because Coll-1 elicits biological effects at sub-nanomolar concentrations (Luo et al., 1993), we predicted that a bona fide Sema III receptor should bind to Sema III with high affinity. To determine the affinity of Sema-AP for neuropilin, neuropilin was transiently expressed in COS cells, and whole cell binding analyses were performed two days later (FIG. 3A). For comparison, the affinity of Sema-AP for its receptor(s) present on NGF-dependent sensory neurons prepared from dissociated E14 DRG was also determined (FIG. 3B). Sema-AP bound to COS cells expressing neuropilin with a high affinity; the calculated equilibrium dissociation constant (KD) was approximately 1.5 nM. There were approximately 125,000 Sema-AP binding sites per COS cell. Interestingly, Sema-AP bound to DRG neurons with an equivalent affinity, and DRG sensory neurons had approximately 20,000 binding sites per cell. These binding affinities are similar to those recently described for netrins and their receptors (Keino-Masu et al., 1996; Leonardo et al., 1997) and Eph receptors and their ligands (Cheng and Flanagan, 1994; Monschau et al., 1997), and they are consistent with a role for neuropilin in Sema III-mediated growth cone collapse and in repulsive guidance of DRG neurons during neurodevelopment. Taken together, these data suggest that neuropilin is a high-affinity Sema III receptor expressed on Sema III-responsive DRG neurons.

Cell Surface Binding Analysis

COS cells were transfected with 2 μg of pMT21-neuropilin, an expression vector encoding neuropilin, or either no DNA or the empty pMT21 expression vector using Lipofectamine (BRL), recovered in growth media, and then grown for 48 hours prior to binding analysis. Dissociated DRG neurons were cultured from E14 DRGs. Briefly, DRG neurons were dissociated in a solution containing trypsin (0.05%), the dissociated neurons were washed to remove trypsin and then plated on collagen-coated tissue culture plates (400,000 cells/35 nm plate). Cells were grown in DRG growth medium (88% MEM, 10% FBS, 0.2% glucose, glutamine (2 mM) and NGF (30 ng/ml)) and subjected to binding analysis four days after plating. Quantitiative cell surface binding was done essentially as described (Flanagan and Leder, 1990).

Figure 4F:
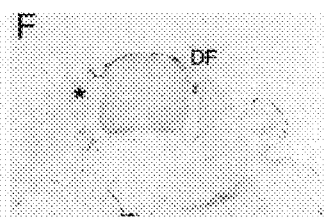
Figure 4G:
Figure 4H:
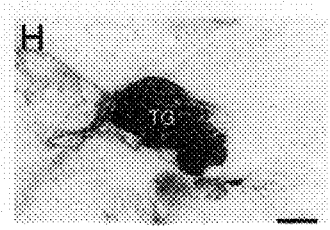

EXAMPLE 3
Neuropilin Antibodies Inhibit Sema III-Mediated Repulsion of DRG Neuron Growth Cones If neuropilin is a receptor for Sema III, then it should be possible to block neuropilin function in NSF-dependent DRG neurons and to prevent Sema III from acting as a repulsive cue. To block neuropilin function, we used our anti-neuropilin antibodies described above. In addition to immunoblotting analysis of extracts of E14 DRG and spinal cord (FIG. 2G), these antibodies were further assessed for specificity by immunostaining sections from E14.5 rat embryos. They specifically reacted with a protein expressed in a subset of neurons including DRG neurons, sympathetic neurons (FIG. 4E), and trigeminal sensory neurons (FIG. 4G). These populations of neurons also express robust levels of neuropilin mRNA as determined by in situ hybridization analysis (FIG. 4H, 6B; (Kawakami et al., 1995)). No immunoreactivity was detected on tissue sections incubated with IgG purified from pre-immune serum (FIG. 4F). In combination with immunoblot analysis, as well as the expression pattern of the other identified member of the neuropilin family (neuropilin-2, see below), these data strongly suggest that these antibodies specifically recognize neuropilin in DRG neurons.

Coculturing E14 DRG and Sema III-expressing COS cells in a collagen matrix provides a robust assay for the chemorepulsive activity of Sema III on these neurons (Messersmith et al., 1995). As seen previously, NGF-dependent DRG neurons were repelled from COS cells that expressed Sema III (FIG. 4A). Including anti-neuropilin antibodies, however, resulted in an inhibition of the repulsive activity of Sema III (FIG. 4B). The amount of axon outgrowth on the side of the DRG adjacent to the Sema III-expressing COS cells was more than two-fold greater in the presence of anti-neuropilin antibodies as compared to cocultures grown in the absence of added antibodies or equal amounts of pre-immune IgG fraction (FIGS. 4C and D; p<0.0001). The results of these antibody perturbation experiments indicate that neuropilin activity is required to mediate the repulsive effects of Sema III on NGF-dependent E14 DRG neurons. Since we have shown that neuropilin is a Sema III binding protein, and since neuropilin is expressed on the axons and growth cones of these neurons, these results demonstrate that neuropilin is an endogenous receptor for Sema III.

In situ Hybridizations

Non-radioactive, digoxigenin (DIG-11-UTP) labeled cRNA probes with either sense or antisense orientation were synthesized by run-off in vitro transcription using T3 and T7 RNA polymerases (Boehringer Mannheim). Probes were generated from three different cDNA templates, rat semaIII cDNA (entire coding region), the extracellular domain of neuropilin (nucleotides 181–2755 of the coding sequence), and a 2.5 kb fragment of neuropilin-2 (downstream of nucleotide 1866). Cryosections (20 μm) of E14.5 rat embryos (plug day was E1) were cut at −15° C. in a Reichert-Jung cryostat and processed for in situ hybridization essentially as described (Giger et al., 1996).

Explant Cocultures and Inhibition of Sema III Activity

E14 DRG and Sema III expressing COS cells were cocultured for 40 hrs as described (Messersmith et al., 1995), except that the culture media was 25% F12 media, 69% OPT-MEM media, 0.04 M glucose, 2 mM glutamine, 0.5% heat inactivated fetal calf serum, and NGF (15 ng/ml) (purified as described (Mobley et al., 1976)). Media was supplemented with either Anti-neuropilin or pre-immune IgG (100 mg/ml). DRG explants and H-sema III-expressing COS cell aggregates were placed ~700 mm apart. For quantification, the region of neurite growth was divided into four quadrants, as diagrammed in FIG. 4C. Neurite outgrowth into the collagen gel was measured from the outer border of each DRG to the perimeter of the bulk of neurites as described (Messersmith et al., 1995). Fixed cocultures were visualized under phase contrast optics on a Zeiss Axiovert 100 inverted microscope and scored blindly by three independent observers. DRG explants with less than 200 mm outgrowth on the distal side were not scored. Statistical analysis was performed using a Student's T-test.

EXAMPLE 4
Neuropilin the First Member of the Neuropilin Gene Family

The great diversity within the semaphorin family of proteins, both with respect to primary amino acid sequence and tissue distribution, led us to investigate the possibility that neuropilin defines a family of conserved semaphorin-binding proteins. A search of the dbEST database identified several human expressed sequence tags that encode proteins either identical to or related to neuropilin. Sequence information from one of these sequence tags was used for the amplification from E14 rat spinal cord/DRG cDNA of a 400 base pair PCR product that was found to encode a portion of a neuropilin-related gene (referred to below as neuropilin-2). This amplification product was used to screen an E14 rat spinal cord/DRG cDNA library. Several cDNAs containing the neuropilin-2 open reading frame were isolated, one of which was sequenced over the entire neuropilin-2 open reading frame (ORF) (see Experimental Procedures).

Conceptual translation of the neuropilin-2 ORF revealed that it encodes a protein that has the same overall extracellular and intracellular organization as neuropilin (FIG. 5A, B). Like neuropilin (Kawakami et al., 1995; Takagi et al., 1991), neuropilin-2 has (N-terminal to C-terminal) a signal sequence, an a1/a2 domain similar to the noncatalytic regions of the complement components C1r and C1s (CUB domain; (Bork and Beckman, 1993)), a b1/b2 domain similar to the C1 and C2 domains of coagulation factors V and VIII, a c region that contains a MAM domain, a transmembrane domain, and a short cytoplasmic domain unique to neuropilins. The length and spacing of these domains in neuropilin and neuropilin-2 are very similar. Neuropilin and neuropilin-2 share 44% amino acid identity over their entire length, however different domains have different degrees of conservation. For example, the a1/a2 and b1/b2 domains are 55 and 44% identical, respectively, whereas the MAM portions of domain c are only 37% identical. Further, the putative transmembrane domains are 71% identical, and the cytoplasmic domains are 53% identical and of the same length. These features clearly show that neuropilin and neuropilin-2 are members of a gene family encoding related proteins, and have implications for their distinct roles in semaphorin signaling.

Neuropilin-2 Identification and Molecular Analysis

A search of the dbEST data base of human expressed sequence tags identified two overlapping clones, GenBank accession numbers AA057388 and AA057680, that displayed sequence similarity to the 3' end of the neuropilin ORF. Degenerate 5' (TTC/TGAA/GGGIGAA/GATA/C/TGGNAAA/GGG (SEQ ID NO: 5); corresponding to the amino acid residues FEGEIGKG (SEQ ID No: 7)) and 3' (NAGT/CTCG/AAAG/ATTG/AATG/ATTT/CTC (SEQ ID NO: 6); corresponding to amino acid residues ENYNFEL (SEQ ID NO: 8)) oligonucleotides were used for PCR-amplication, using 10 ng of E14 rat spinal cord/DRG cDNA and employing 45 amplification cycles (96° C. 1 min.; 50° C. 1 min.; 72° C. 1 min.). Amplification products were cloned into pCRII (Invitrogen) and sequenced. One 400 base pair (bp) amplification product encoded a neuropilin-related sequence and was used to screen a rat E14 DRG/spinal cord Lambda Zap II (Stratagene) cDNA library. Several positive clones were isolated, and one 6 kb clone was found to contain the entire neuropilin-2 ORF. 3371 bp of this clone, including the neuropilin ORF, were sequenced on both strands. Alignment of neuropilin and neuropilin-2 sequences was performed using Gene Works (Intelligenetics).

Figures 6A, 6B, 6C:
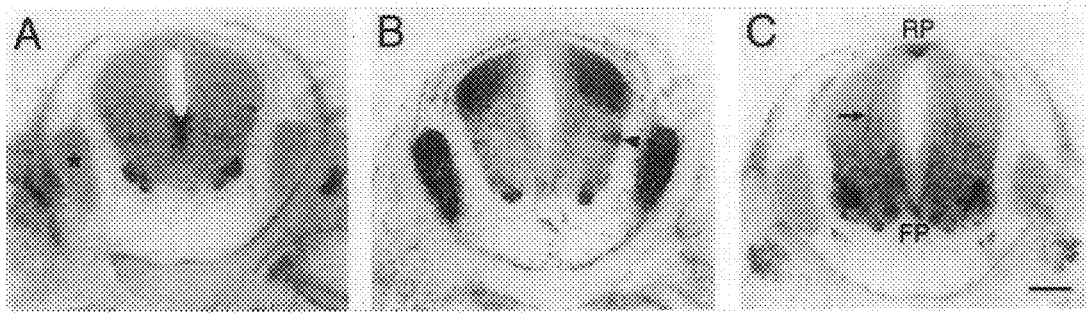
FIGS. 6A–6C. Neuropilin and neuropilin-2 are expressed in distinct populations of cells within the spinal cord and DRG. In situ hybridization of cross-sections of E14.5 rat spinal cord with DIG labeled cRNA probes specific for semaphorin III (FIG. 6A), neuropilin (FIG. 6B), and neuropiln-2 (FIG. 6C).

EXAMPLE 5
Neuropilin and Neuropilin-2 are Expressed in Distinct Populations of Neurons in the Developing Rat Spinal Cord The existence of neuropilin-2 is consistent with the hypothesis that there are multiple, structurally-related semaphorin receptors. Because neuropilin is present in discrete populations of neurons (Kawakami et al., 1995), and because individual semaphorins have distinct neuronal expression patterns (Adams et al., 1996; Giger et al., 1996; Luo et al., 1995; Puschel et al., 1995; Shepherd et al., 1996; Wright et al., 1995; Zhou et al., 1997), we compared the patterns of expression of neuropilin and neuropilin-2 by in situ hybridization. Cross-sections of E14.5 rat embryos stained for the presence of neuropilin mRNA displayed discrete labeling in the spinal cord and a subset of DRG neurons (FIG. 6B), consistent with previous observations of neuropilin expression (Kawakami et al., 1995). For comparison, sema III spinal cord expression is shown in FIG. 6A. In the ventral spinal cord, strong neuropilin expression was observed in motor pools and in a thin stripe of cells in the intermediolateral column. Weaker neuropilin expression was detected in the dorsal horn. Neuropilin expression was not seen in the spinal neuroepithelium. In contrast, a very different expression pattern was observed for neuropilin-2 (FIG. 6C). Unlike neuropilin, which is strongly expressed in DRG, neuropilin-2 expression was not detected in neurons within the DRG. Moreover, staining in the spinal cord was largely confined to the ventral horn, the intermediate grey, and a thin dorsally extending stripe of cells at the border of the neuroepithelium. Robust neuropilin-2 expression was seen in the lateral motor pools of the ventral cord and lateral part of the basal plate neuroepithelium. The roof plate and the floor plate also showed moderate neuropilin-2 expression. Examination of other CNS structures revealed that neuropilin and neuropilin-2 are expressed in overlapping, but distinct, populations of neurons. For example, expression of neuropilin, but not neuropilin-2, was detected in the trigeminal ganglion (FIG. 4, data not shown). However, expression of neuropilin-2, but not neuropilin, was observed in the accessory olfactory bulb (data not shown). Lastly, as has been observed for neuropilin, neuropilin-2 expression was not restricted to the nervous system. Strong non-neuronal expression of neuropilin-2 was detected in several tissues, including the mesenchymal tissue lining the ribs (data not shown). Together, these results demonstrate that neuropilin and neuropilin-2 are expressed in overlapping yet distinct populations of neurons in the CNS, and that both genes are expressed in neuronal as well as non-neuronal cells.

References (Each of which is Expressly Incorporated by, Reference Herin)

Ackerman, S. L., Kozak, L. P., Przyborski, S. A., Rund, L. A., Boyer, B. B., and Knowles, B. B. (1997). The mouse rostral cerebellar malformation gene encodes an UNC-5-like protein. Nature 386, 838–842.

Adams, R. H., Betz, H., and Puschel, A. W. (1996). A novel class of murine semaphorins with homology to thrombospondin is differentially expressed during early embryogenesis. Mech. Dev. 57, 33–45.

Beckmann, G., and Bork, P. (1993). An adhesive domain detected in functionally diverse receptors. Trends Biochem. Sci. 18, 40–41.

Behar, O., Golden, J. A., Mashimo, H., Schoen, F. J., and Fishman, M. C. (1996),. Semaphorin III is needed for normal patterning and growth of nerves, bones, and heart. Nature 383, 525–528.

Bork, P., and Beckman, G. (1993). The CUB domain: A widespread module in developmentally regulated proteins. J. Mol. Biol. 231, 539–545.

Cleng, H.-J., and Flanagan, J. G. (1994). Identification and cloning of ELF-1, a developmentally expressed ligand for the Mek4 and Sek receptor tyrosine kinases. Cell 79, 157–168.

Fan, J., and Raper, J. A. (1995). Localized collapsing cues can steer growth cones without inducing their full collapse. Neuron 14, 263–274.

Fan, J., Mansfield, S. G., Redman, T., Phillip, R., Gordon-Weeks, P. R., and Raper, J. A. (1993). The organization of F-actin and microtubules in growth cones exposed to a brain-derived collapsing factor. J. Cell Biol. 121, 867–878.

Fazeli, A., Dickinson, S. L., Herminston, M. L., Tighe, R. V., Steen, R. G., Small, C. G., Stoeckli, E. T., Keino-Masu, K., Masu, M., Rayburn, H., Simons, J., Bronson, R. T., Gordon, J. I., Tessier-Lavigne, M., and Weinberg, R. A. (1997). Phenotype of mice lacking functional Deleted in colorectal cancer (Dcc) gene. Nature 386, 796–804.

Fitzgerald, M., Kwiat, G. C., Middleton, J., and Pini, A. (1993). Ventral spinal chord inhibition of neurite outgrowth from embryonic rat dorsal root ganglia. Development 117, 1377–1384.

Flanagan, J. G., and Leder, P. (1990). The kit ligand: A cell surface molecule altered in Steel mutant fibroblasts. Cell 63, 185–194.

Giger, R. J., Wolfer, D. P., De Wit, G. M. J., and Verhaagen, J. (1996). Anatomy of rat semaphorin III/collapsin-1 mRNA expression and relationship to developing nerve tracts during neuroembryogenesis. J. Comp. Neurol. 375, 378–392.

Ginty, D. D., Bonni, A., and Greenberg, M. E. (1994). Nerve growth factor activates a Ras-dependent protein kinase that stiulates c-fos transcription via phosphorylation of CREB. Cell 77, 713–725.

Goshima, Y., Nakamura, F., Strittmatter, P., and Strittmatter, S. M. (1995). Collapsin-induced growth cone collapse mediated by an intracellular protein related to UNC-33. Nature 376, 509–514.

He, Z., and Tessier-Lavigne, M. (1997). Molecular basis of axonal chemorepulstion: Neuropilin is a semaphorin/collapsin receptor. Cell, this issue.

Hirata, T., Takagi, S., and Fujisawa, H. (1993). The membrane protein A5, a putative neuronal recognition molecule, promotes neurite outgrowth. Neurosci. Res. 17, 159–169.

Ip, N. Y., and Yancopoulos, G. D. (1996). The neurotrophins and CNTF: Two families of collaborative neurotrophic factors. Ann. Rev. Neurosci. 19, 491–515.

Ivains, J. K, Raper, J. A., and Pittman, R. N. (1991). Intracellular calcium levels do not change during contact-mediated collapse of chick DRG growth cone structure. J. Neurosci. 11, 1597–1608.

Kawakami, A., Kitsukawa, T., Takagi, S., and Fujisawa, H. (1995). Developmentally regulated expression of a cell surface protein, neuropilin, in mouse nervous system. J. Neurobiol. 29, 1–17.

Keynes, R., and Cook, G. M. W. (1995). Axon guidance molecules. Cell 83, 161–169.

Kindt, R. M., and Lander, A. D. (1995). Pertussis toxin specifically inhibits growth cone guidance by a mechanism independent of direct G protein inactivation. Neuron 15, 79–88.

Kitsukawa, T., Shimono, A., Kawakami, A., Kondoh, H., and Fugisawa, H. (1995). Overexpression of a membrane protein, neuropilin, in chimeric mice causes anomalies in the cardiovascular system, nervous system and limbs. Development 121, 4309–4318.

Kolodkin, A. L. (1996). Semaphorins: mediators of repulsive growth cone guidance. Trends Cell Biol. 6, 15–22.

Kolodkin, A. L., Matthes, D., and Goodman, C. S. (1993). The semaphorin genes encode a family of transmembrane and secreted growth cone guidance molecules. Cell 75, 1389–1399.

Kolodkin, A. L., Matthes, D., O'Connor, T., Patel, N. H., Admon, A., Bentley, D., and Goodman, C. S. (1992). Fasciclin IV: Sequence, expression, and function during growth cone guidance in the grasshopper embryo. Neuron 9, 831–835.

Leonardo, E. D., Hinck, L., Masu, M., Keino-Masu, K., Ackerman, S. L., and Tessier-Lavigne, M. (1997). Vertebrate homologues of C. elegans UNC-5 are candidate netrin receptors. Nature 386, 833–838.

Luo, Y., Raible, D., and Raper, J. A. (1993). Collapsin: a protein in brain that induces the collapse and paralysis of neuronal growth cones. Cell 75, 217–227.

Luo, Y., Shepherd, I., Li, J., Renzi, M. J., Chang, S., and Raper, J. (1995). A family of molecules related to collapsin in the embryonic click nervous system. Neuron 14, 1131–1140.

Matthes, D. J., Sink, H., Kolodkin, A. L., and Goodman, C. S. (1995). Semaphorin II can function as a selective inhibitor of specific synaptic arborizations in Drosophila. Cell 81, 631–639.

McIntire, S. L., Garriga, G., White, J., Jacobson, D., and Horvitz, H. R. (1992). Genes necessary for directed axonal elongation or fasciculation in C. elegans. Neuron 8, 307–322.

Messersmith, E. K., Leonardo, E. D., Shatz, C. J., Tessier-Lavigne, M., Goodman, C. S., and Kolodkin, A. L. (1995). Semaphorin III can function as a selective chemorepellent to pattern sensory projections in the spinal cord. Neuron 14, 949–959.

Mobley, W. C., Schenker, A., and Shooter, E. M. (1976). Characterization and isolation of proteolytically modified nerve growth factor. Biochem. 15, 5543–5551.

Monschau, B., Kremoser, C., Ohta, K., Tanaka, H., Kaneko, T., Yamada, T., Hardwerker, C., Hornberger, M. R., Loschinger, J., Pasquale, E. B., Siever, D. A., Verderame, M. F., Muller, B. K., Bonhoeffer, F., and Drescher, U. (1997). Shared and distinct functions of RAGS and Elf-1 in guiding retinal axons. EMBO J. 16, 1258–1267.

Pearson, A., Lux, A., and Krieger, M. (1995). Expression cloning of dSR-CI, a class C macrophage-specific scavenger receptor from Drosophila melanogaster. Proc. Natl. Acad. Sci. USA 92, 4065–4060.

Puschel, A. W. (1996). The Semaphorins. A family of axonal guidance molecules? Euro. J. Neurosci 8, 1317–1321.

Puschel, A. W., Adams, R. H., and Betz, H. (1995). Murine semaphorin D/collapsin is a member of a diverse gene family and creates domains inhibitory for axonal extension. Neuron 14, 941–948.

Puschel, A. W., Adams, R. H., and Betz, H. (1996). The sensory innervation of the mouse spinal cord may be patterned by differential expression of and differential responsiveness to semaphorins. Mol. Cell. Neurosci. 7, 419–431.

Sambrook, J., Fritsch, E. F., and Maniatis, T. (1989). Molecular Cloning: A Laboratory Manual, Second Edition (Cold Spring Harbor, N.Y.: Cold Spring Harbor Laboratory).

Satoda, M., Takagi, S., Ohta, K., Hirata, T., and Fujisawa, H. (1995). Differential expression of two cell surface proteins, neuropilin and plexin, in Xenopus olfactory axon subclasses. J. Neurosci. 15, 942–955.

Serafini, T., Kennedy, T., Galko, M., Mirzayan, C., Jessell, T., and Tessier-Lavigne, M. (1994). The netrins define a family of axon outgrowth-promoting proteins with homology to C. Elegans UNC-6. Cell 78, 409–424.

Shepherd, I. T., Luo, Y., Lefcort, F., Reichardt, L. F., and Raper, J. A. (1997). A sensory axon repellent secreted from ventral spinal cord explants is neutralized by antibodies raised against collapsin-1. Development 124, 1377–1385.

Shepherd, I. T., Luo, Y., Raper, J. A., and Chang, S. (1996). The distribution of collapsin-1 mRNA in the developing chick nervous system. Dev. Biol. 173, 185–199.

Shirasaki, R., Tamada A., Katsumata, R., and Murakami, F. (1995). Guidance of cerebellofugal axons in the rat embryo: Directed growth toward the floor plate and subsequent elongation along the longitudinal axis. Neuron 14, 961–972.

Takagi, S., Hirata, T., Agata, K., Mochii, M., Eguchi, G., and Fujisawa, H. (1991). The A5 antigen, a candidate for the neuronal recognition molecule, has homologies to complement components and coagulation factors. Neuron 7, 295–307.

Takagi, S., Kasuya, Y., Shimizu, M., Matsuura, T., Tsuboi, M., Kawakami, A., and Fujisawa, H. (1995). Expression of a cell adhesion molecule, neuropilin, in the developing chick nervous system. Dev. Biol. 170, 207–222.

Takagi, S., Tsuji, T., Amagai, T., Takamatsu, T., and Fujisawa, H. (1987). Specific cell surface labels in the visual center of Xenopus laevis tadpole identified using monoclonal antibodies. Dev. Biol. 122, 90–100.

Tessier-Lavigne, M., and Goodman, C. S. (1996). The molecular biology of axon guidance. Science 274, 1123–1133.

Varela-Echavarria, A., Tucker, A., Puschel, A. W., and Guthrie, S. (1997). Motor axon subpopulations respond differentially to the chemorepellents netrin-1 and semaphorin D. Neuron 18, 193–207.

Wang, L.-H., and Strittmatter, S. M. (1996). A family of rat CRMP genes is differentially expressed in the nervous system. J. Neurosci. 16, 6197–6207.

Wright, D. E., White, F. A., Gerfen, R. W., Silos-Santiago, I., and Snider, W. D. (1995). The guidance molecule semaphorin III is expressed in regions of spinal cord and periphery avoided by growing sensory axons. J. Comp. Neurol. 361, 321–333.

Zhou, L., White, F. A., Lentz, S. I., Wright, D. E., Fisher, D. A., and Snider, W. D. (1997). Cloning and expression of a novel murine semaphorin with structural similarity to insect semaphorin I. Mol. Cell. Neurosci. 9, 26–41.

What is claimed is:

1. A method of monitoring the interaction of a semaphorin and a neuropilin according to SEQ ID NO: 2 or 4, comprising the steps of:

contacting a first isolated protein which comprises an extracellular domain of the neuropilin with a second isolated protein which comprises an extracellular domain of a semaphorin under conditions where the extracellular domain of the neuropilin binds to the extracellular domain of the semaphorin; and determining the binding of the first protein to the second protein or the second protein to the first protein.

2. The method of claim 1 wherein the step of determining comprises:

contacting the first and second proteins with an antibody which specifically binds to the first protein or the second protein to form an immunoprecipitate;

determining the presence of the first protein in the immunoprecipitate if an antibody which specifically binds to the second protein was used, and determining the presence of the second protein in the immunoprecipitate if an antibody which specifically binds to the first protein was used.

3. The method of claim 1 wherein the first or second protein is bound to a solid support.

4. The method of claim 1 wherein the first protein lacks a transmembrane and an intracellular domain of the neuropilin.

5. The method of claim 1 wherein one of the two proteins is myc-tagged and an anti-myc antibody is used.

6. The method of claim 1 wherein one of the two proteins is a fusion protein comprising an enzyme which produces a readily detectable product in the presence of substrate.

7. The method of claim 6 wherein the enzyme is alkaline phosphatase.

8. The method of claim 1 wherein a test compound is added to the first and second proteins to determine its effect on binding of the first protein to the second protein.

9. The method of claim 1 wherein the neuropilin is neuropilin-1 having SEQ ID NO:4.

10. The method of claim 1 wherein the neuropilin is neuropilin-2 having SEQ ID NO:2.

11. The method of claim 1 wherein the semaphorin is semaphorin III.

12. A method for monitoring the interaction between a semaphorin and a neuropilin, comprising the steps of:

contacting a protein comprising a semaphorin sema or Ig basic domain with cells which are transfected with an expression construct encoding a polypeptide comprising an extracellular domain of the neuropilin according to SEQ ID NO: 2 or 4 so that the cells express the polypeptide; and detecting the protein comprising the semaphorin sema or Ig basic domain which binds to the cells.

13. The method of claim 12 wherein the protein comprising the semaphorin domain is a fusion protein.

14. The method of claim 12 further comprising the step of:

prior to the step of contacting, determining that the cells express the extracellular domain of neuropilin.

15. The method of claim 12 wherein the semaphorin is semaphorin III.

16. The method of claim 12 wherein the polypeptide is neuropilin-1 having SEQ ID NO:4.

17. The method of claim 12 wherein the polypeptide is neuropilin-2 having SEQ ID NO:2.

18. The method of claim 13 wherein the fusion protein further comprises alkaline phosphatase.

19. The method of claim 18 wherein a substrate for alkaline phosphatase is added which forms a colored product.

20. The method of claim 12 wherein the cells are COS cells.

21. The method of claim 1 wherein a test compound which binds to the first protein is added to the first and second proteins to determine its effect on binding of the first protein to the second protein.

22. A method of monitoring the interaction of a semaphorin and a neuropilin according to SEQ ID NO: 2 or 4, comprising the steps of:

contacting (a) a first isolated protein which comprises an extracellular domain of the neuropilin, wherein the first isolated protein lacks a transmembrane domain and an intracellular domain of the neuropilin with (b) a second isolated protein which comprises an extracellular domain of a semaphorin under conditions where the extracellular domain of the neuropilin binds to the extracellular domain of the semaphorin, wherein the first or second isolated protein is bound to a solid support;

adding a test compound to the first and second isolated proteins;

determining the binding of the first isolated protein to the second isolated protein or the second isolated protein to the first isolated protein in the presence and absence of the test compound.

23. The method of claim 12 wherein the cells do not naturally express neuropilins.

24. The method of claim 22 wherein the neuropilin is neuropilin-1 having SEQ ID NO:4.

25. The method of claim 22 wherein the neuropilin is neuropilin-2 having SEQ ID NO:2.

* * * * *